(12) United States Patent  
Joseph et al.

(10) Patent No.: US 10,517,749 B2  
(45) Date of Patent: *Dec. 31, 2019

(54) ORTHOPEDIC BACK BRACE

(71) Applicant: DJO, LLC, Vista, CA (US)

(72) Inventors: Mark Joseph, Aspen, CO (US); Kristian Gamble, Minneapolis, MN (US); Colleen Ankeny, Grasston, MN (US)

(73) Assignee: DJO, LLC, Vista, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 15/599,233

(22) Filed: May 18, 2017

(65) Prior Publication Data

US 2017/0348134 A1 Dec. 7, 2017

Related U.S. Application Data

(63) Continuation of application No. 13/674,613, filed on Nov. 12, 2012, now Pat. No. 9,655,761.

(51) Int. Cl.  
*A61F 5/02* (2006.01)

(52) U.S. Cl.  
CPC .................................. *A61F 5/028* (2013.01)

(58) Field of Classification Search  
CPC .... A61F 5/028; A61F 2250/006; A61F 5/024; A61F 13/04; A61F 5/01; A61F 5/0585;

(Continued)

(56) References Cited

U.S. PATENT DOCUMENTS

| 57,283 A | 8/1866 | Brown |
|---|---|---|
| D19,360 S | 10/1889 | Sanders |

(Continued)

FOREIGN PATENT DOCUMENTS

| CN | 2902232 | 5/2007 |
|---|---|---|
| CN | 101279110 | 10/2008 |

(Continued)

OTHER PUBLICATIONS

Johnson & Johnson Orthoplast Splinting Materials, http://www.medco-school.com/Supply/Product.asp?Leaf_Id-80365, archived 2007.

(Continued)

*Primary Examiner* — Ophelia A Hawthorne  
(74) *Attorney, Agent, or Firm* — Knobbe Martens Olson & Bear LLP

(57) ABSTRACT

Orthopedic braces and associated methods are described for treatment of lower back injuries and chronic back pain. An orthopedic brace may include a pair of back panels, a pair of front panels, and a closure system. A lateral end of each front panel is releasably coupleable to a lateral end of each back panel at a desired angle. A ventral end of each front panel includes an attachment provision configured to allow one of the front panels to releasably attach to the other of the front panels generally over an abdomen of a wearer. The brace also includes a pocket on the ventral end of at least one of the front panels, the pocket configured to temporarily receive a hand of the wearer to aid in donning the orthopedic brace.

20 Claims, 16 Drawing Sheets

(58) Field of Classification Search
CPC .......... A61F 5/0118; A61F 5/026; A61F 5/03; A61F 13/14
See application file for complete search history.

(56) References Cited

U.S. PATENT DOCUMENTS

| | | |
|---|---|---|
| 482,647 A | 9/1892 | Obear |
| D35,545 S | 12/1901 | Schaefer |
| 911,243 A | 2/1909 | Johannesen |
| 975,734 A | 11/1910 | Tebeau |
| 1,082,542 A | 12/1913 | Manson |
| 1,360,840 A | 11/1920 | White |
| 1,477,070 A | 3/1922 | Martin |
| 1,471,948 A | 10/1923 | Cox et al. |
| 1,583,606 A | 5/1926 | Roussel |
| 2,070,810 A | 2/1937 | Saling |
| 2,181,689 A | 11/1939 | Bell |
| 2,206,404 A | 7/1940 | Jones |
| 2,477,040 A | 3/1945 | Brown et al. |
| 2,554,337 A | 5/1951 | Lampert |
| 2,736,314 A | 2/1956 | Hale |
| 2,759,475 A | 8/1956 | Swaay |
| 2,818,063 A | 12/1957 | Smith et al. |
| 2,904,040 A | 9/1959 | Hale |
| D198,069 S | 4/1964 | Connelly |
| D203,018 S | 11/1965 | Helferich |
| 3,230,952 A | 1/1966 | Reyes Terron |
| 3,302,642 A | 2/1967 | Allen |
| 3,306,284 A | 2/1967 | McKinley |
| 3,313,297 A | 4/1967 | Applegate et al. |
| 3,320,950 A | 5/1967 | McElvenny |
| 3,420,231 A | 1/1969 | Edenbaum |
| 3,490,444 A | 1/1970 | Larson |
| 3,512,523 A | 5/1970 | Barnett |
| 3,692,023 A | 9/1972 | Phillips et al. |
| 3,788,307 A | 1/1974 | Kistner |
| 3,896,843 A | 7/1975 | Millar et al. |
| 3,906,943 A | 9/1975 | Arluck |
| 3,916,885 A | 11/1975 | Gaylord, Jr. |
| 3,924,272 A | 12/1975 | Allen et al. |
| 4,006,741 A | 2/1977 | Arluck |
| 4,019,505 A | 4/1977 | Wartman |
| 4,136,686 A | 1/1979 | Arluck |
| 4,169,469 A | 10/1979 | Arluck |
| 4,193,395 A | 3/1980 | Gruber |
| D256,055 S | 7/1980 | Finnieston |
| 4,235,228 A | 11/1980 | Gaylord et al. |
| 4,240,415 A | 12/1980 | Wartman |
| D259,955 S | 7/1981 | Helferich |
| 4,286,586 A | 9/1981 | Potts |
| 4,316,457 A | 2/1982 | Liegeois |
| D266,288 S | 9/1982 | Coon |
| 4,379,463 A | 4/1983 | Meier et al. |
| D270,284 S | 8/1983 | Lindh et al. |
| 4,427,002 A | 1/1984 | Baron et al. |
| 4,441,711 A | 4/1984 | Dubar et al. |
| 4,442,834 A | 4/1984 | Tucker et al. |
| 4,454,873 A | 6/1984 | Laufenberg et al. |
| 4,471,993 A | 9/1984 | Watson |
| 4,473,671 A | 9/1984 | Green |
| 4,483,333 A | 11/1984 | Wartman |
| 4,510,927 A | 4/1985 | Peters |
| 4,531,241 A | 7/1985 | Berger |
| 4,572,167 A | 2/1986 | Brunswick |
| 4,584,993 A | 4/1986 | Nelson |
| 4,600,618 A | 7/1986 | Raychok, Jr. et al. |
| D287,640 S | 1/1987 | Primiano |
| 4,661,535 A | 4/1987 | Borroff |
| 4,726,361 A | 2/1988 | Farley |
| 4,765,319 A | 8/1988 | Finnieston et al. |
| 4,770,299 A | 9/1988 | Parker |
| 4,784,123 A | 11/1988 | Robeson |
| 4,827,915 A | 5/1989 | Gorsen |
| 4,872,448 A | 10/1989 | Johnson |
| 4,888,225 A | 12/1989 | Sandvig et al. |
| 4,912,174 A | 3/1990 | Grouiller |
| 4,946,726 A | 8/1990 | Sandvig et al. |
| 4,955,368 A | 9/1990 | Heimann |
| 5,031,607 A | 7/1991 | Peters |
| 5,038,759 A | 8/1991 | Morgenstern |
| 5,058,576 A | 10/1991 | Grim et al. |
| D326,719 S | 6/1992 | Eghamn |
| 5,158,098 A | 10/1992 | Jalalian |
| 5,180,361 A | 1/1993 | Moore et al. |
| 5,230,698 A | 7/1993 | Garth |
| 5,316,604 A | 5/1994 | Fell |
| RE34,714 E | 8/1994 | Burns et al. |
| 5,364,693 A | 11/1994 | Moren et al. |
| 5,366,439 A | 11/1994 | Peters |
| D357,745 S | 4/1995 | Radwell |
| 5,409,761 A | 4/1995 | Langley |
| 5,415,622 A | 5/1995 | Kelley |
| D363,780 S | 10/1995 | Darby et al. |
| 5,454,780 A | 10/1995 | Duback et al. |
| 5,520,529 A | 5/1996 | Heckel |
| D373,639 S | 9/1996 | McKie |
| 5,554,104 A | 9/1996 | Grim |
| 5,599,288 A | 2/1997 | Shirley et al. |
| 5,624,386 A | 4/1997 | Tailor et al. |
| 5,632,722 A | 5/1997 | Tweardy et al. |
| 5,688,229 A | 11/1997 | Bauer |
| 5,737,774 A | 4/1998 | Petty-Saphon et al. |
| 5,752,873 A | 5/1998 | Morris |
| 5,752,926 A | 5/1998 | Larson et al. |
| D395,514 S | 6/1998 | Stano |
| 5,763,047 A | 6/1998 | Green |
| 5,769,804 A | 6/1998 | Harris et al. |
| 5,807,291 A | 9/1998 | Larson et al. |
| 5,819,312 A | 10/1998 | Snyder et al. |
| 5,823,984 A | 10/1998 | Silverberg |
| 5,826,304 A | 10/1998 | Carlson |
| 5,830,167 A | 11/1998 | Jung |
| D405,180 S | 2/1999 | Reina |
| 5,865,778 A | 2/1999 | Johnson |
| 5,882,322 A | 3/1999 | Kim et al. |
| 5,902,259 A | 5/1999 | Wilkerson |
| 5,926,843 A | 7/1999 | Winchester |
| 5,934,599 A | 8/1999 | Hammerslag |
| 5,951,504 A | 9/1999 | Iglesias et al. |
| 5,971,946 A | 10/1999 | Quinn et al. |
| 5,982,285 A | 11/1999 | Bueche et al. |
| 6,042,557 A | 3/2000 | Ferguson et al. |
| 6,053,884 A | 4/2000 | Peters |
| 6,056,671 A | 5/2000 | Marmer |
| 6,056,713 A | 5/2000 | Hayashi |
| RE36,745 E | 6/2000 | Rudy, Jr. et al. |
| 6,093,161 A | 7/2000 | Vlaeyen et al. |
| 6,110,134 A | 8/2000 | Clark, Jr. et al. |
| 6,146,240 A | 11/2000 | Morris |
| D436,177 S | 1/2001 | Miller |
| 6,168,966 B1 | 1/2001 | Grim et al. |
| 6,179,798 B1 | 1/2001 | Nelson |
| D437,416 S | 2/2001 | Slautterback |
| 6,186,966 B1 | 2/2001 | Grim et al. |
| 6,202,953 B1 | 3/2001 | Hammerslag |
| 6,254,560 B1 | 7/2001 | Tweardy et al. |
| 6,289,558 B1 | 9/2001 | Hammerslag |
| 6,322,529 B1 | 11/2001 | Chung |
| 6,325,772 B1 | 12/2001 | Scheuermann et al. |
| 6,358,220 B1 | 3/2002 | Langen et al. |
| 6,416,074 B1 | 7/2002 | Maravets et al. |
| 6,423,020 B1 | 7/2002 | Koledin |
| D463,565 S | 9/2002 | Slautterback |
| 6,509,078 B1 | 1/2003 | Beckmann |
| 6,520,925 B1 | 2/2003 | Thibodo, Jr. |
| D473,653 S | 4/2003 | Weaver, II et al. |
| D477,088 S | 7/2003 | Brown et al. |
| D477,409 S | 7/2003 | Mills et al. |
| D477,410 S | 7/2003 | Wiggins et al. |
| 6,602,215 B1 | 8/2003 | Richie, Jr. |
| 6,663,581 B1 | 12/2003 | Calabrese |
| D492,787 S | 7/2004 | Weaver, II et al. |
| 6,779,282 B2 | 8/2004 | Grohninger |
| D496,465 S | 9/2004 | Weaver, II |

(56) References Cited

U.S. PATENT DOCUMENTS

| | | |
|---|---|---|
| D500,855 S | 1/2005 | Pick et al. |
| 6,843,190 B1 | 1/2005 | LaPierre-McAfee |
| 6,872,188 B2 | 3/2005 | Caille et al. |
| D505,727 S | 5/2005 | Krahner et al. |
| 6,893,410 B1 | 5/2005 | Hely |
| 6,922,917 B2 | 8/2005 | Kerns et al. |
| 6,960,176 B1 | 11/2005 | Hely et al. |
| 7,001,348 B2 | 2/2006 | Garth et al. |
| D518,895 S | 4/2006 | Weaver, II et al. |
| D519,211 S | 4/2006 | Doty et al. |
| 7,025,737 B2 | 4/2006 | Modglin |
| 7,041,073 B1 | 5/2006 | Patron |
| 7,056,298 B1 | 6/2006 | Weber |
| 7,082,701 B2 | 8/2006 | Dalgaard et al. |
| 7,083,585 B2 | 8/2006 | Latham |
| 7,090,653 B2 | 8/2006 | Moeller |
| D530,016 S | 10/2006 | Sroufe et al. |
| 7,141,031 B2 | 11/2006 | Garth et al. |
| 7,182,741 B2 | 2/2007 | Porrata et al. |
| 7,204,817 B1 | 4/2007 | Toronto et al. |
| D542,919 S | 5/2007 | Leatt |
| 7,217,060 B2 | 5/2007 | Ingimarsson |
| D550,370 S | 9/2007 | Peters et al. |
| D552,743 S | 10/2007 | Verkade et al. |
| D552,744 S | 10/2007 | Verkade et al. |
| D558,883 S | 1/2008 | Ortiz |
| 7,316,660 B1 | 1/2008 | Modglin |
| 7,329,229 B2 | 2/2008 | Scheinberg et al. |
| D565,189 S | 3/2008 | Gramza et al. |
| 7,392,602 B2 | 7/2008 | Reagan et al. |
| 7,399,288 B2 | 7/2008 | Chao |
| D580,064 S | 11/2008 | Lin et al. |
| D580,555 S | 11/2008 | Lin et al. |
| 7,449,006 B2 | 11/2008 | Wolanske |
| 7,470,243 B2 | 12/2008 | Garth |
| D584,822 S | 1/2009 | Weber |
| 7,507,215 B2 | 3/2009 | Ryan |
| 7,591,050 B2 | 9/2009 | Hammerslag |
| 7,597,671 B2 | 10/2009 | Baumgartner et al. |
| 7,608,052 B1 | 10/2009 | Baker |
| 7,645,250 B2 | 1/2010 | Koby et al. |
| 7,674,234 B2 | 3/2010 | Calco et al. |
| D616,556 S | 5/2010 | Hu |
| D617,464 S | 6/2010 | Weaver, II et al. |
| 7,727,172 B2 | 6/2010 | Wang |
| D626,242 S | 10/2010 | Sagnip et al. |
| D626,244 S | 10/2010 | Sagnip et al. |
| D628,300 S | 11/2010 | Caden |
| D628,696 S | 12/2010 | Robertson |
| D629,115 S | 12/2010 | Robertson |
| 7,846,118 B2 | 12/2010 | Sandhu |
| 7,854,714 B1 | 12/2010 | Weber et al. |
| 7,874,997 B2 | 1/2011 | Jaccard |
| D632,401 S | 2/2011 | Stevens |
| 7,883,485 B2 | 2/2011 | Moenning et al. |
| D633,622 S | 3/2011 | Chiang |
| D633,623 S | 3/2011 | Leatt et al. |
| D635,269 S | 3/2011 | Franke et al. |
| D635,270 S | 3/2011 | Chiang |
| D635,682 S | 4/2011 | Chiang |
| D636,494 S | 4/2011 | Garth et al. |
| D638,948 S | 5/2011 | Janzon |
| 7,942,837 B2 | 5/2011 | Clark et al. |
| 7,950,112 B2 | 5/2011 | Hammerslag et al. |
| D639,965 S | 6/2011 | Wehsely-Swiczinsky |
| 7,954,204 B2 | 6/2011 | Hammerslag et al. |
| 7,955,287 B2 | 6/2011 | Frangi |
| D641,482 S | 7/2011 | Robertson et al. |
| D641,483 S | 7/2011 | Robertson et al. |
| D643,978 S | 8/2011 | Abajo Alonso et al. |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| D649,648 S | 11/2011 | Cavalieri et al. |
| D649,649 S | 11/2011 | Leatt et al. |
| D649,650 S | 11/2011 | Wehsely-Swiczinsky |
| 8,057,417 B2 | 11/2011 | Imai |
| D650,485 S | 12/2011 | Jaccard |
| D652,937 S | 1/2012 | Robertson et al. |
| 8,091,182 B2 | 1/2012 | Hammerslag et al. |
| D654,180 S | 2/2012 | Weaver, II |
| D657,062 S | 4/2012 | Chiang |
| D657,063 S | 4/2012 | Chiang |
| D663,850 S | 7/2012 | Joseph |
| D663,851 S | 7/2012 | Joseph |
| D663,852 S | 7/2012 | Joseph |
| D664,259 S | 7/2012 | Joseph |
| D665,088 S | 8/2012 | Joseph |
| D666,301 S | 8/2012 | Joseph |
| D666,302 S | 8/2012 | Joseph |
| 8,246,560 B2 | 8/2012 | Gaylord et al. |
| 8,277,401 B2 | 10/2012 | Hammerslag et al. |
| 8,303,527 B2 | 11/2012 | Joseph |
| D687,566 S | 8/2013 | Joseph |
| 8,856,972 B2 | 10/2014 | Kirshon |
| 8,951,217 B2 | 2/2015 | Joseph |
| 9,295,748 B2 | 3/2016 | Joseph |
| 9,408,738 B2 | 8/2016 | Boraas et al. |
| 9,561,128 B2 | 2/2017 | Joseph |
| 9,655,761 B2 * | 5/2017 | Joseph ............... A61F 5/028 |
| 2002/0068890 A1 | 6/2002 | Schwenn et al. |
| 2002/0095750 A1 | 7/2002 | Hammerslag |
| 2002/0148461 A1 | 10/2002 | Heinz et al. |
| 2002/0161114 A1 | 10/2002 | Gunatillake et al. |
| 2003/0178404 A1 | 9/2003 | Dimartino et al. |
| 2003/0204938 A1 | 11/2003 | Hammerslag |
| 2004/0024337 A1 | 2/2004 | Tseng et al. |
| 2004/0034316 A1 | 2/2004 | Castro |
| 2005/0033207 A1 | 2/2005 | Anders |
| 2005/0034686 A1 | 2/2005 | Spatt |
| 2005/0043664 A1 | 2/2005 | Reaux |
| 2005/0101898 A1 | 5/2005 | Cohen |
| 2005/0197606 A1 | 9/2005 | Preire |
| 2005/0251074 A1 | 11/2005 | Latham |
| 2005/0273030 A1 | 12/2005 | Koby et al. |
| 2005/0281999 A1 | 12/2005 | Hofmann et al. |
| 2006/0051402 A1 | 3/2006 | Bogardus et al. |
| 2006/0052730 A1 | 3/2006 | Hargrave et al. |
| 2006/0062991 A1 | 3/2006 | Sendijarevic et al. |
| 2006/0129075 A1 | 6/2006 | Scheinberg et al. |
| 2006/0155226 A1 | 7/2006 | Grim et al. |
| 2006/0156517 A1 | 7/2006 | Hammerslag et al. |
| 2006/0173390 A1 | 8/2006 | Van Wyk et al. |
| 2007/0004993 A1 | 1/2007 | Coppens et al. |
| 2007/0077393 A1 | 4/2007 | Chiang et al. |
| 2007/0179417 A1 | 8/2007 | Schwenn et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0082033 A1 | 4/2008 | Ortiz |
| 2008/0083135 A1 | 4/2008 | Hammerslag et al. |
| 2008/0177210 A1 | 7/2008 | McDevitt Larson |
| 2008/0262400 A1 | 10/2008 | Clark et al. |
| 2009/0082707 A1 | 3/2009 | Rumsey |
| 2009/0192425 A1 | 7/2009 | Garth et al. |
| 2009/0192427 A1 | 7/2009 | Brown et al. |
| 2009/0204042 A1 | 8/2009 | Park |
| 2009/0204047 A1 | 8/2009 | MacArthur |
| 2009/0264802 A1 | 10/2009 | Chen |
| 2010/0168630 A1 | 7/2010 | Cropper et al. |
| 2010/0185130 A1 | 7/2010 | Rizo Patron |
| 2010/0262054 A1 | 10/2010 | Summit et al. |
| 2010/0268139 A1 | 10/2010 | Garth |
| 2010/0268140 A1 | 10/2010 | Berlese |
| 2010/0268141 A1 | 10/2010 | Bannister |
| 2010/0299959 A1 | 12/2010 | Hammerslag et al. |
| 2010/0318010 A1 | 12/2010 | Sandifer et al. |
| 2011/0034844 A1 | 2/2011 | Thorgilsdottir et al. |
| 2011/0082402 A1 | 4/2011 | Oddou et al. |
| 2011/0130694 A1 | 6/2011 | Livolsi et al. |
| 2011/0213284 A1 | 9/2011 | Garth et al. |
| 2011/0313389 A1 | 12/2011 | Wood et al. |

(56) References Cited

U.S. PATENT DOCUMENTS

| | | |
|---|---|---|
| 2012/0065562 A1 | 3/2012 | Kaphingst |
| 2015/0119775 A1 | 4/2015 | Gildersleeve et al. |
| 2015/0238343 A1 | 8/2015 | Joseph |
| 2016/0317342 A1 | 11/2016 | Joseph |
| 2017/0014216 A1 | 1/2017 | Boraas et al. |
| 2017/0189241 A1 | 7/2017 | Joseph |

FOREIGN PATENT DOCUMENTS

| | | |
|---|---|---|
| EP | 0 393 003 | 10/1990 |
| EP | 0 401 883 | 12/1990 |
| EP | 0 619 102 | 10/1994 |
| EP | 0 625 342 | 11/1994 |
| EP | 0 795 307 | 4/2004 |
| JP | 09-234241 | 9/1997 |
| JP | 2004-065912 | 3/2004 |
| WO | WO 93/21967 | 11/1993 |
| WO | WO 07/035875 | 3/2007 |
| WO | WO 10/099130 | 9/2010 |
| WO | WO 11/071264 | 6/2011 |
| WO | WO 12/138523 | 10/2012 |

OTHER PUBLICATIONS

Aquaplast Splinting Materials, http://www.wisdomking.com/aquaplast-splinting, archived 2008.
ISR and WO dated Feb. 21, 2014 in PCT/US13/69200.
Extended European Search Report dated Jul. 8, 2016 in related European patent application No. 13853605.7.

\* cited by examiner

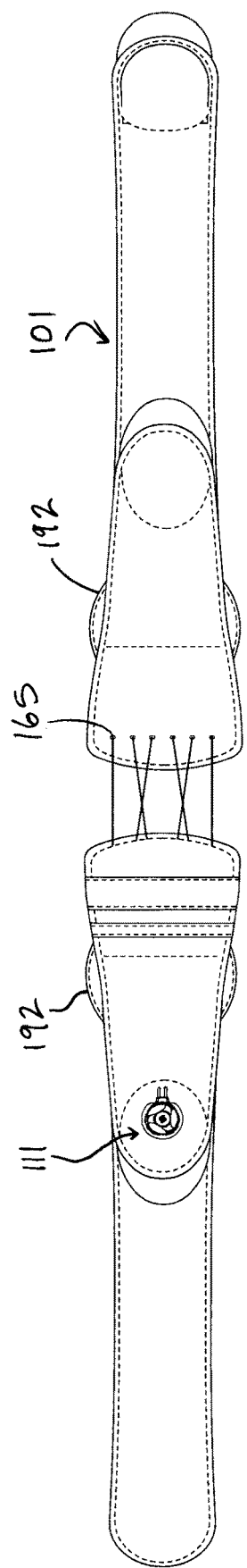
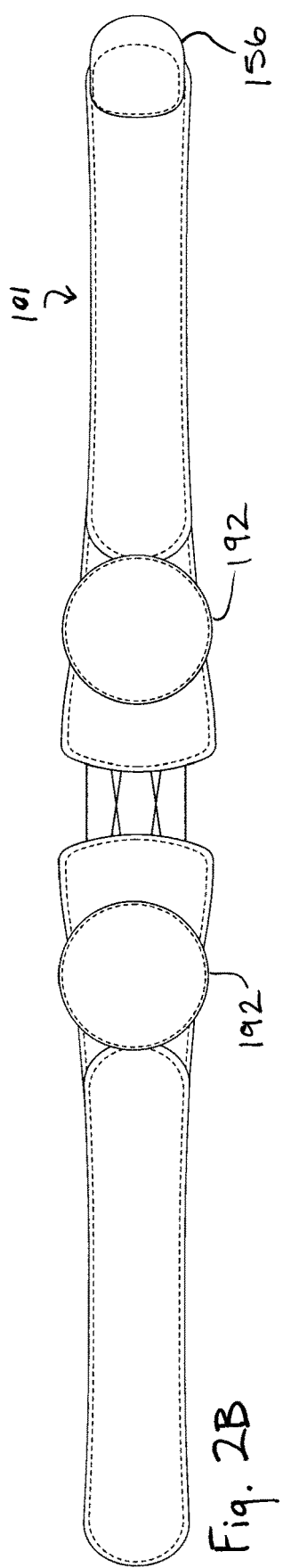
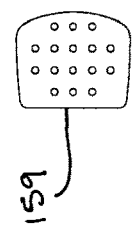
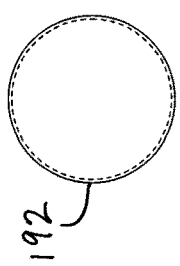
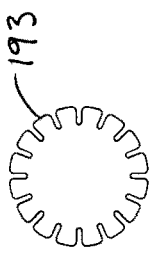

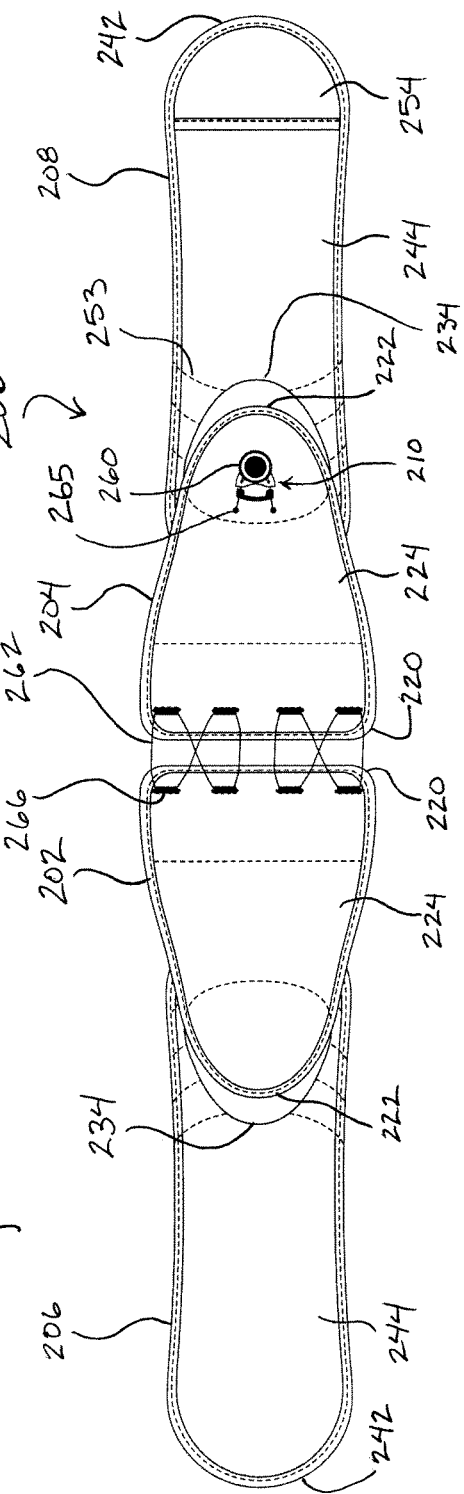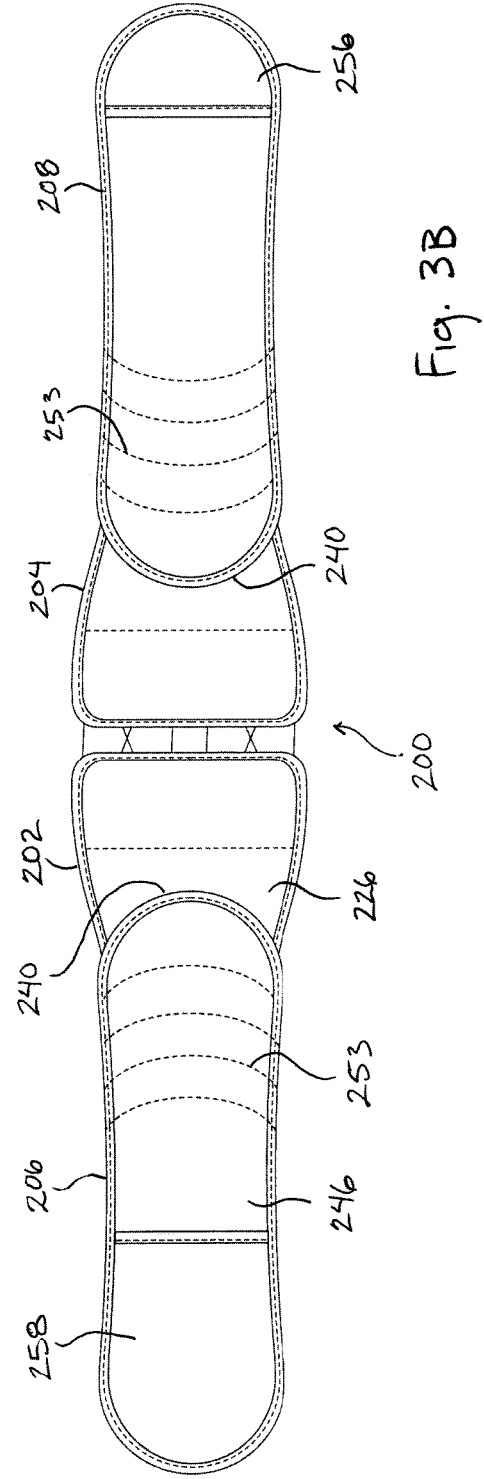

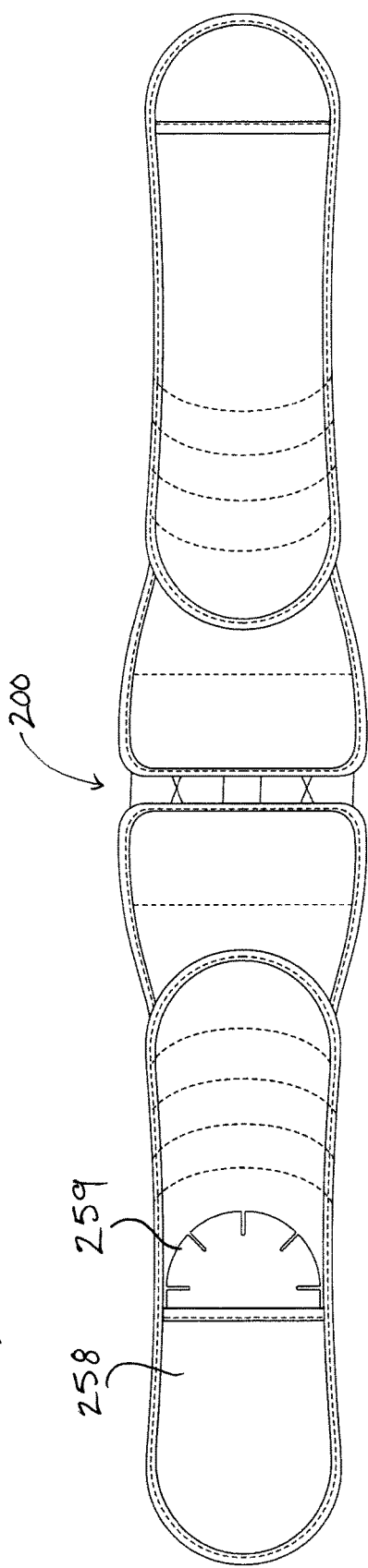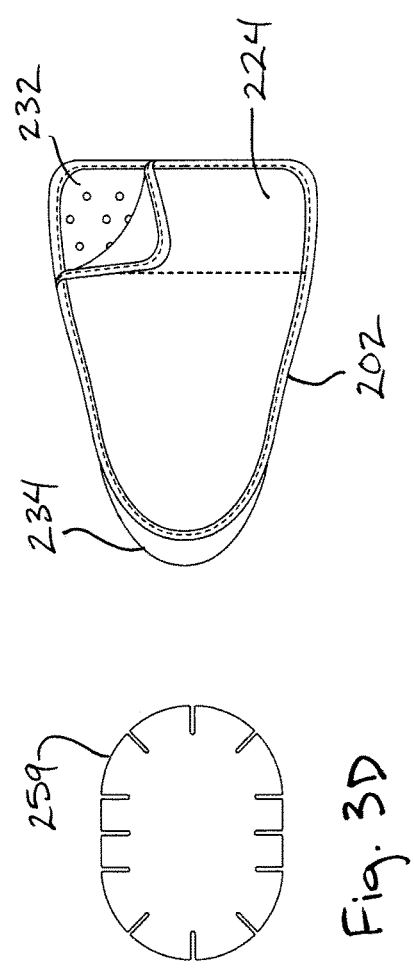

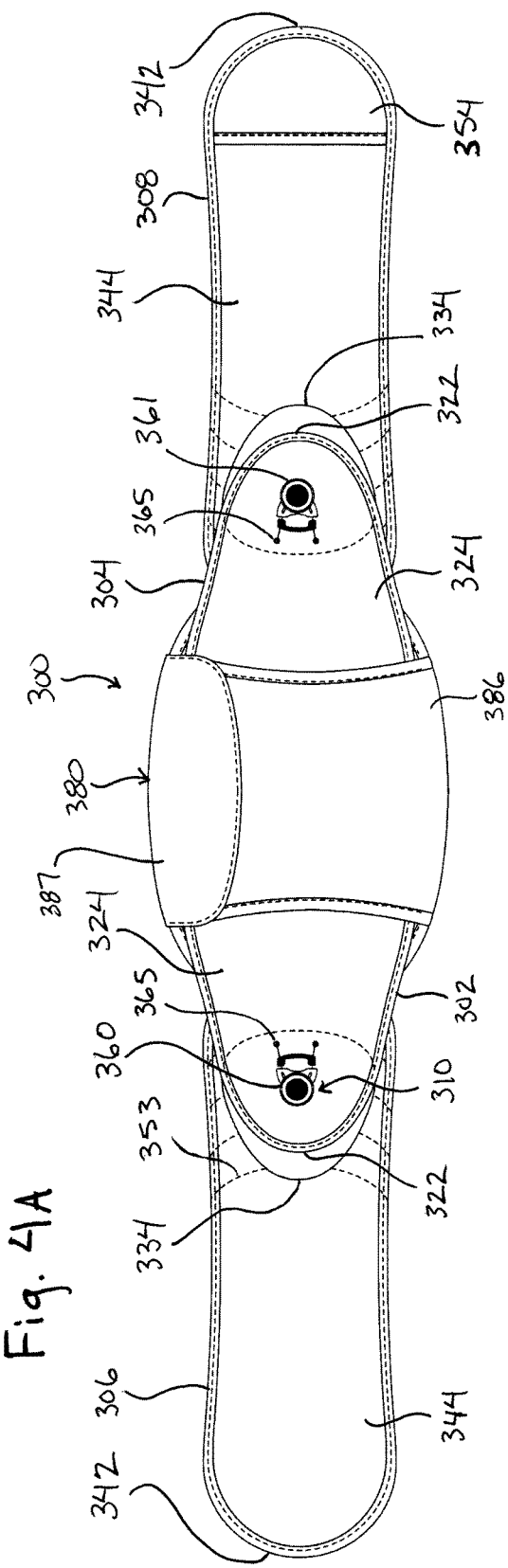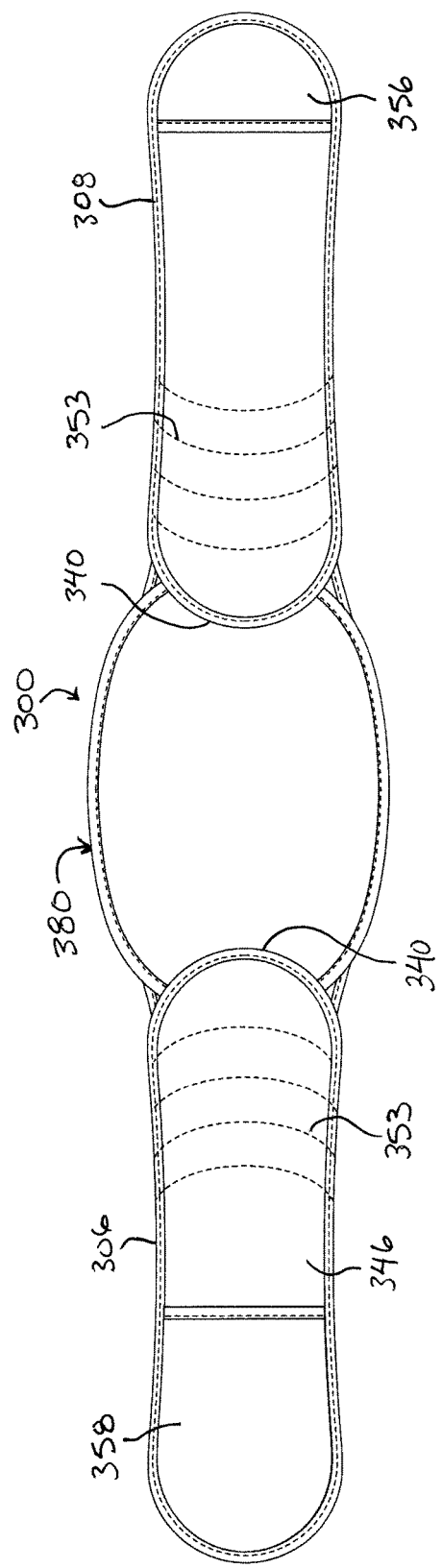

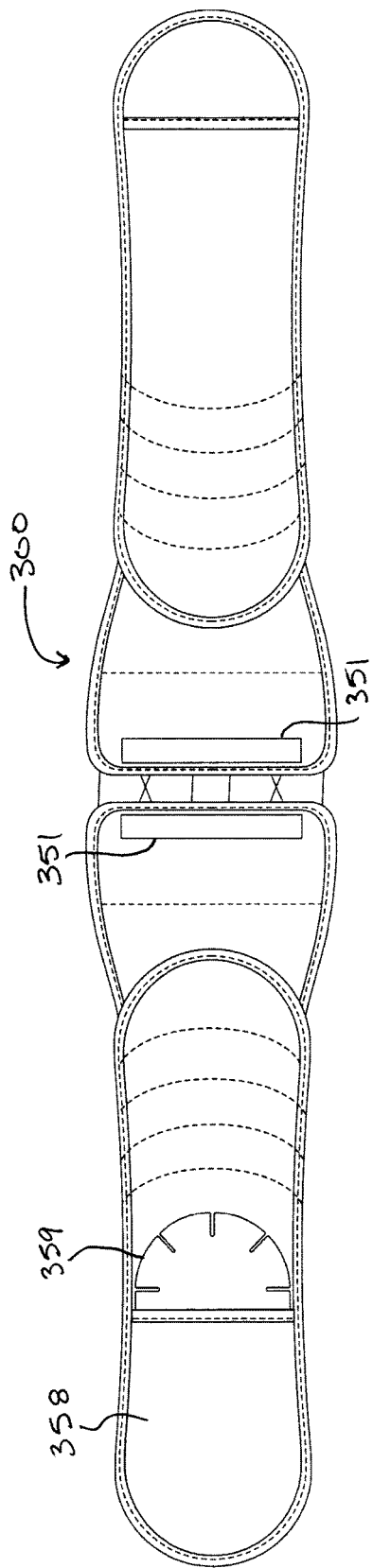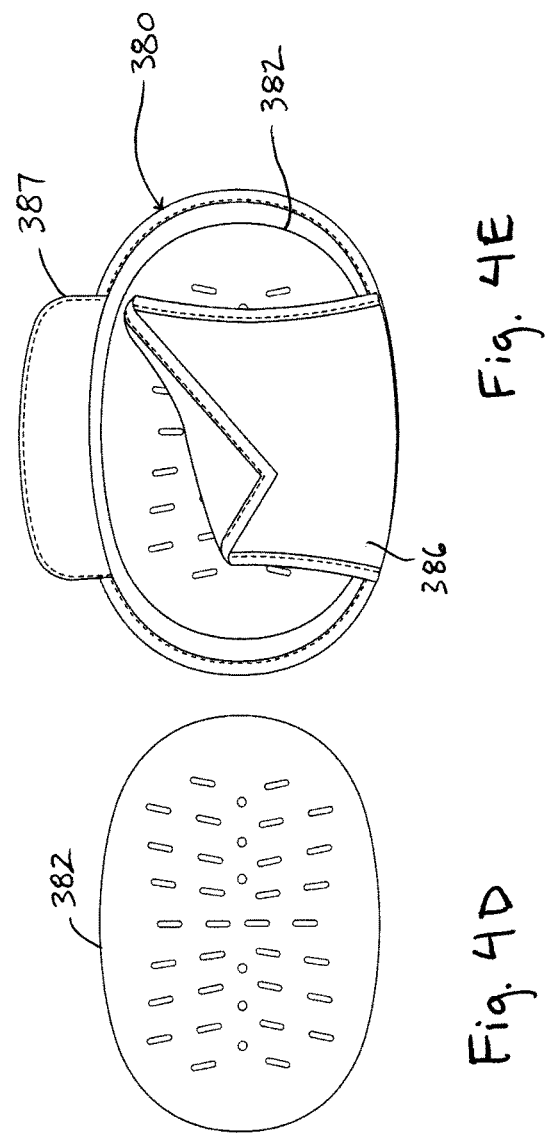

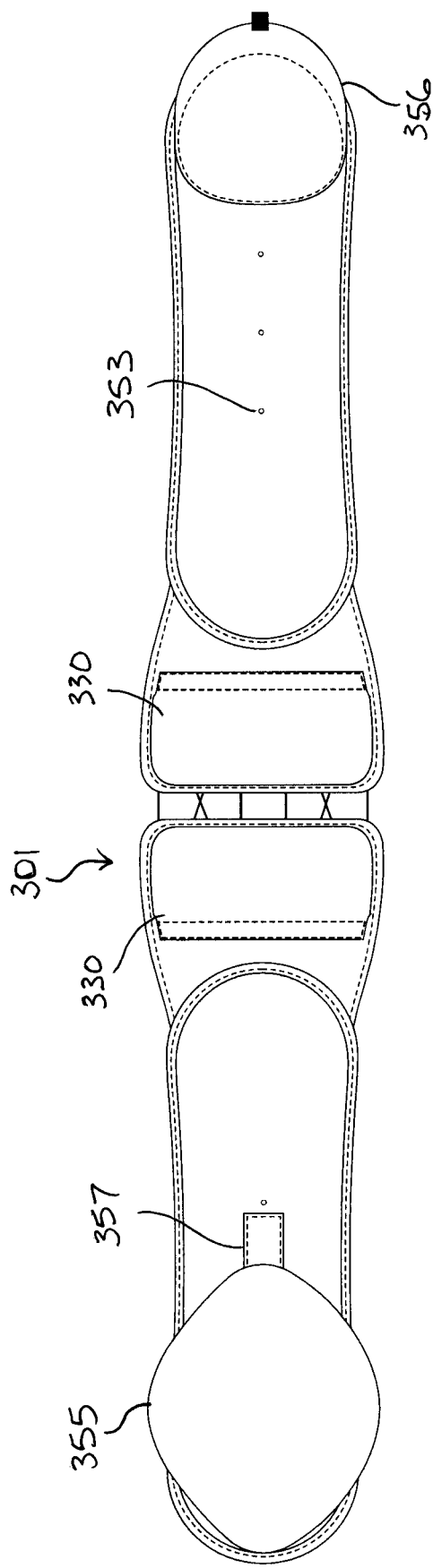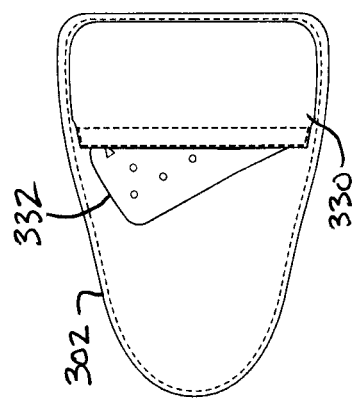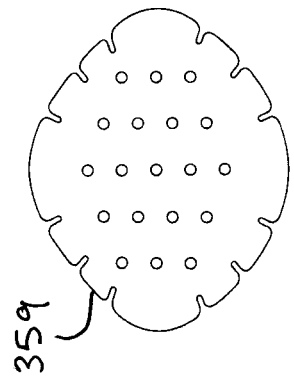

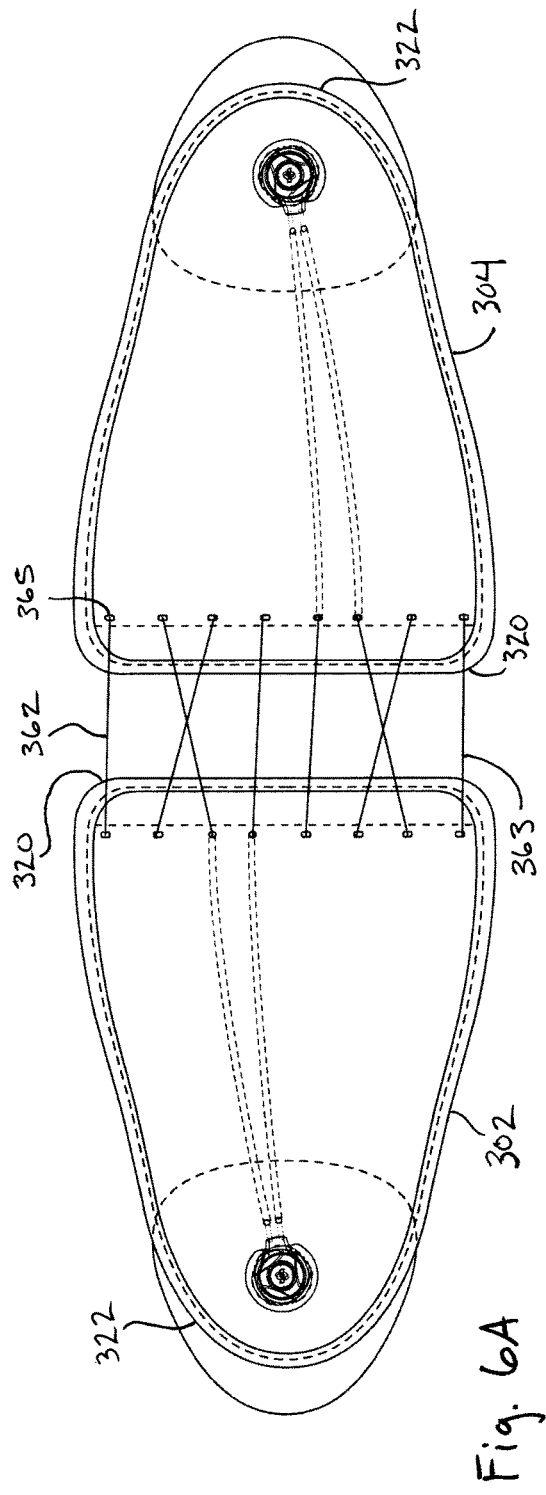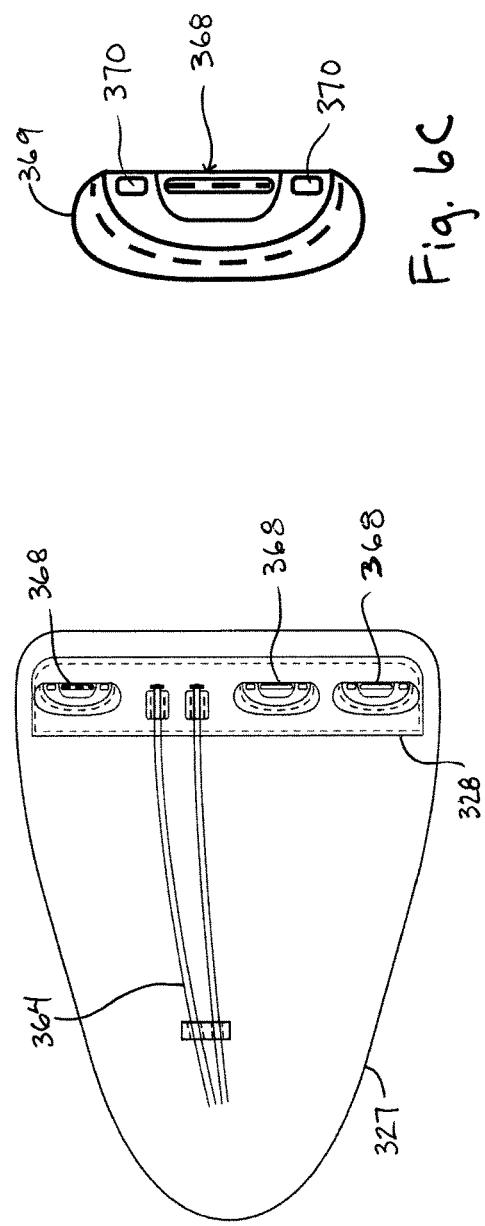

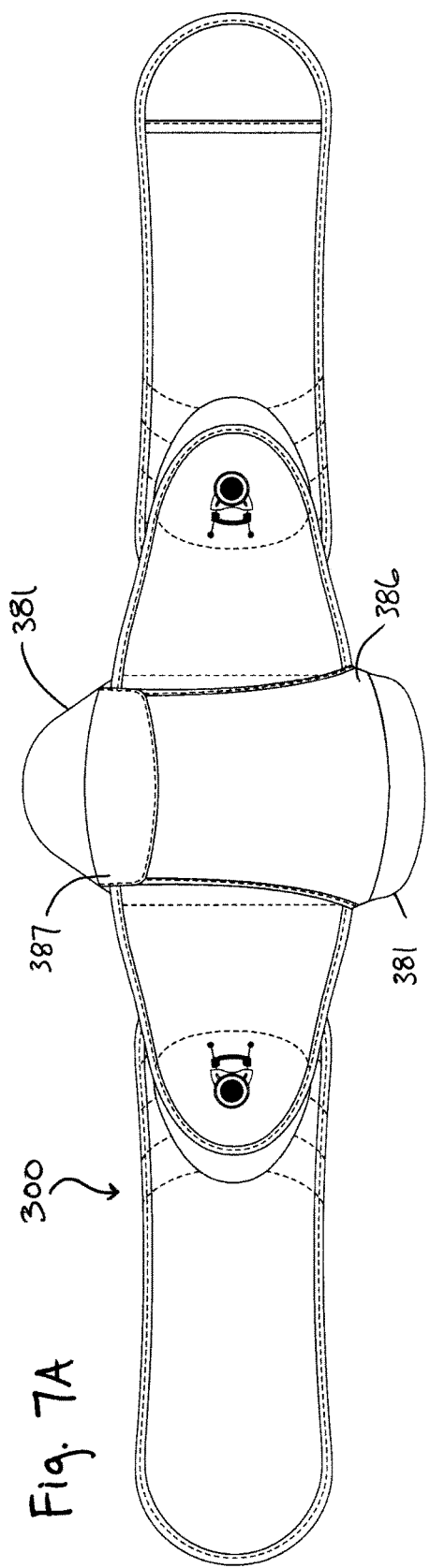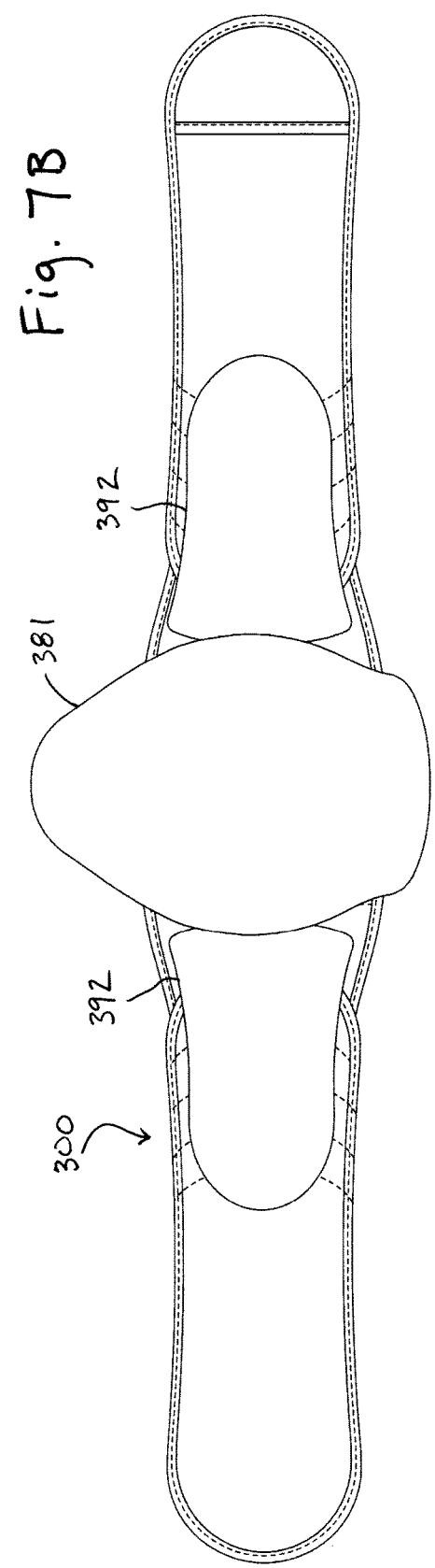

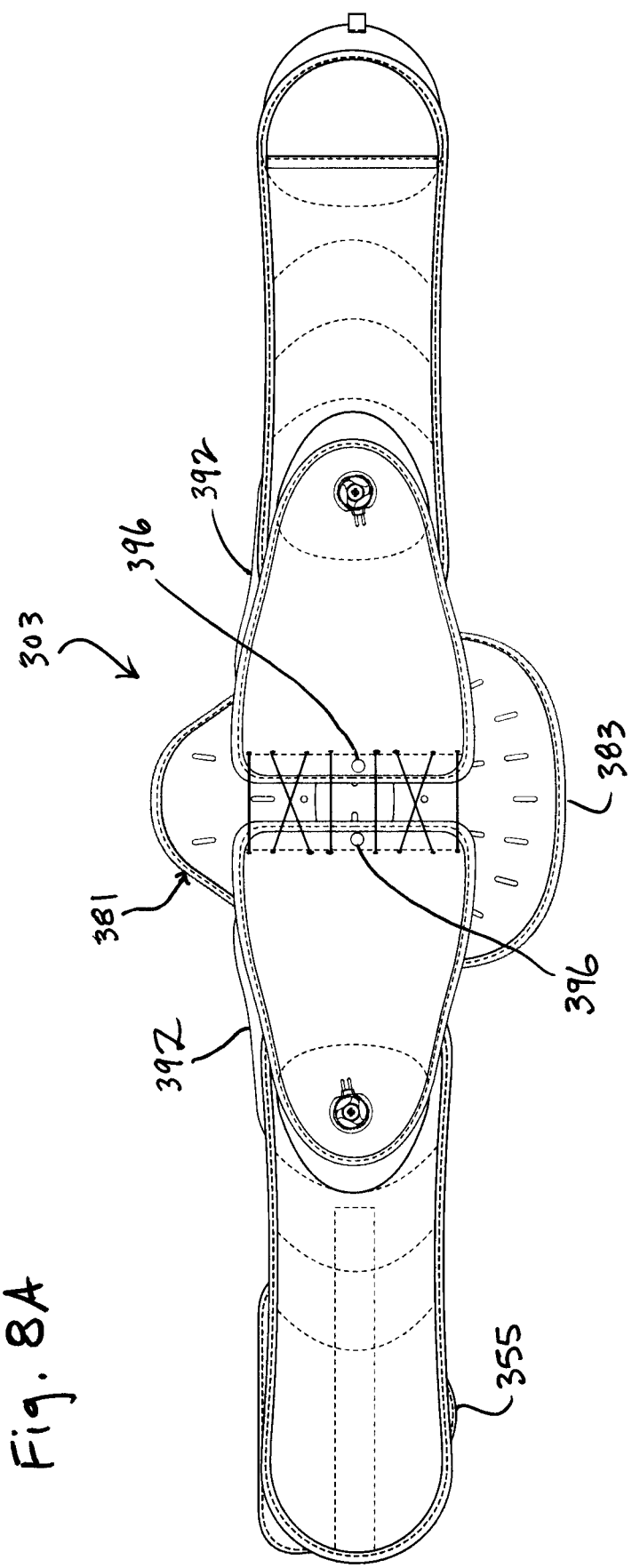

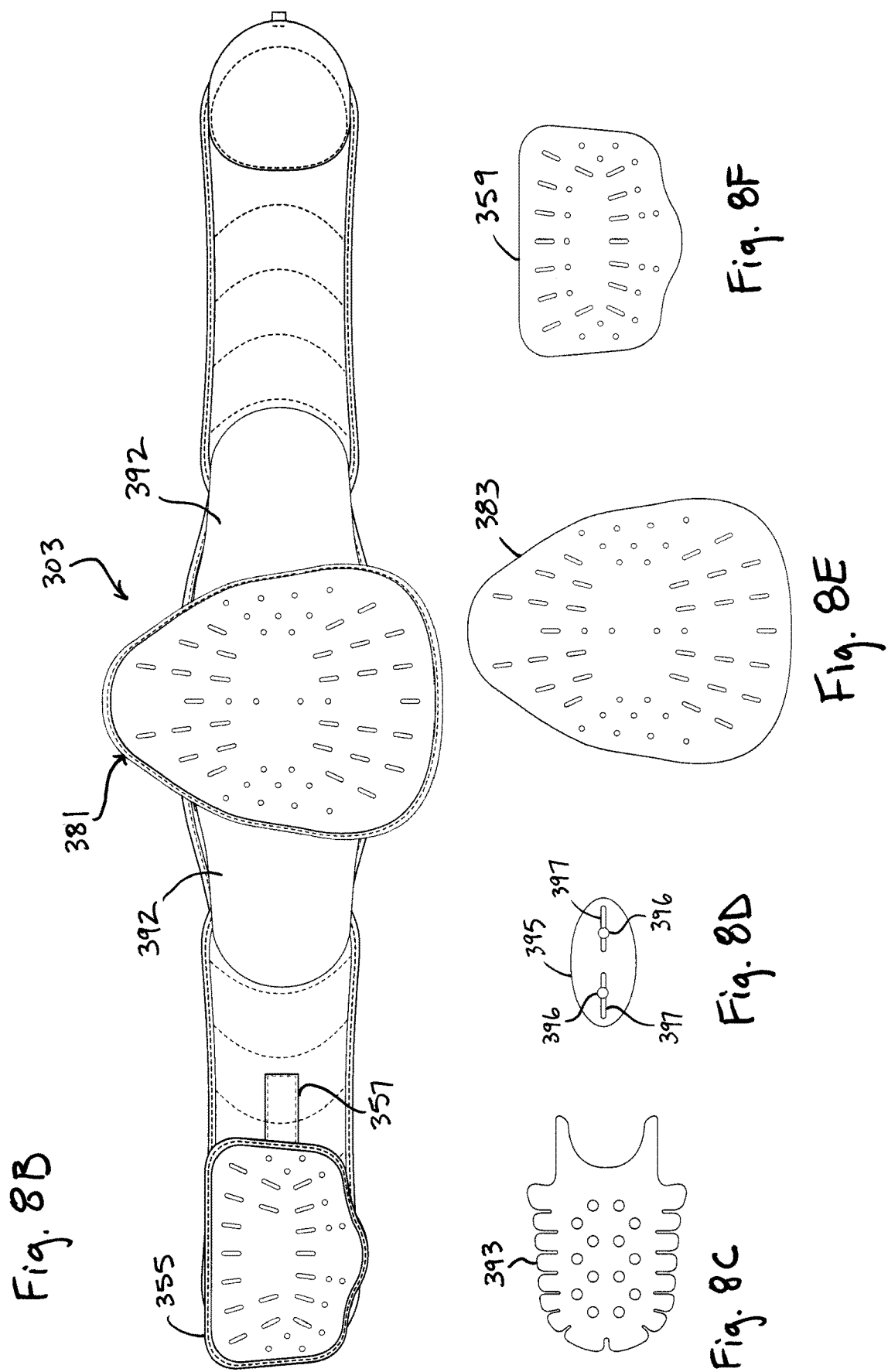

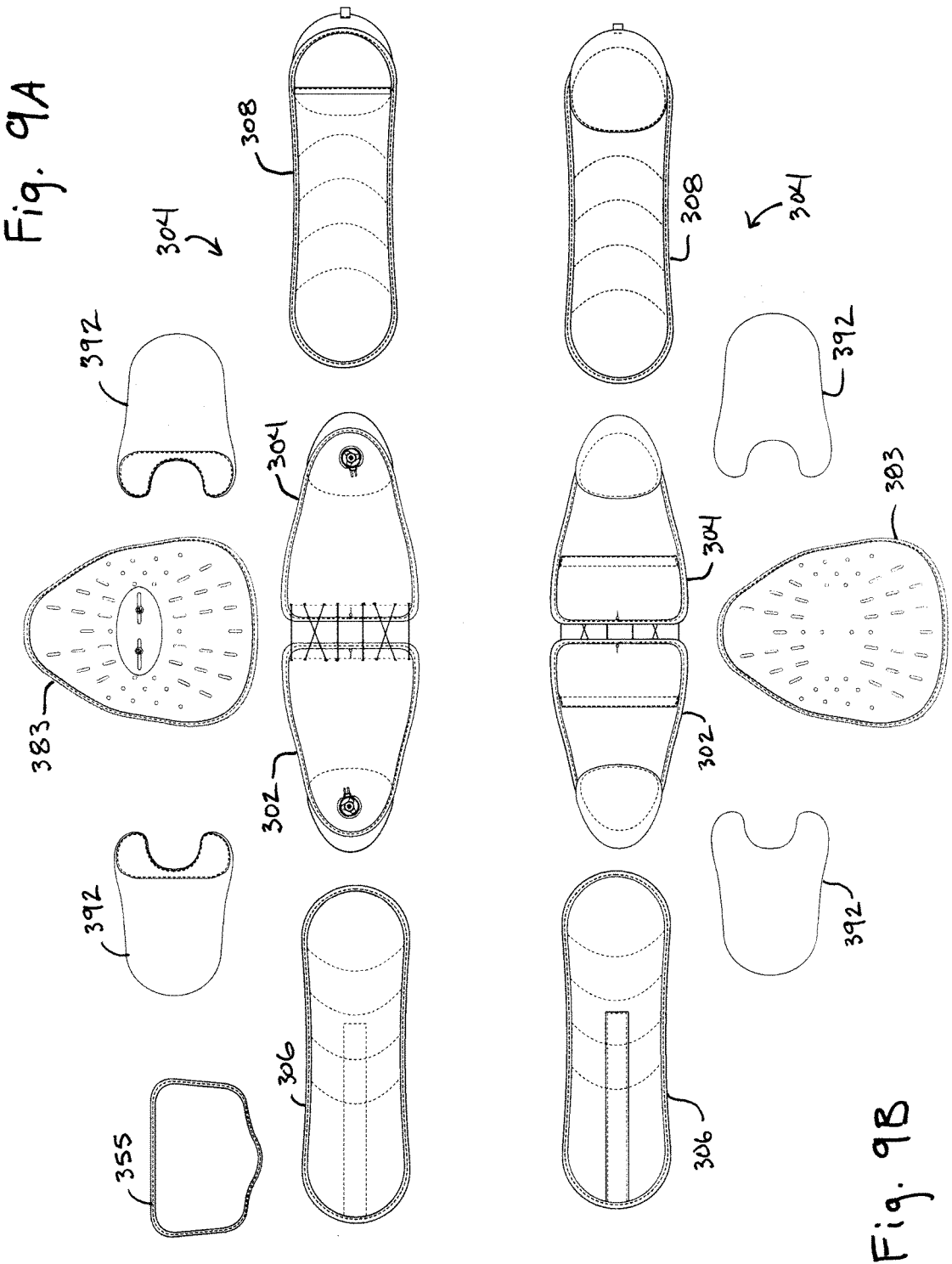

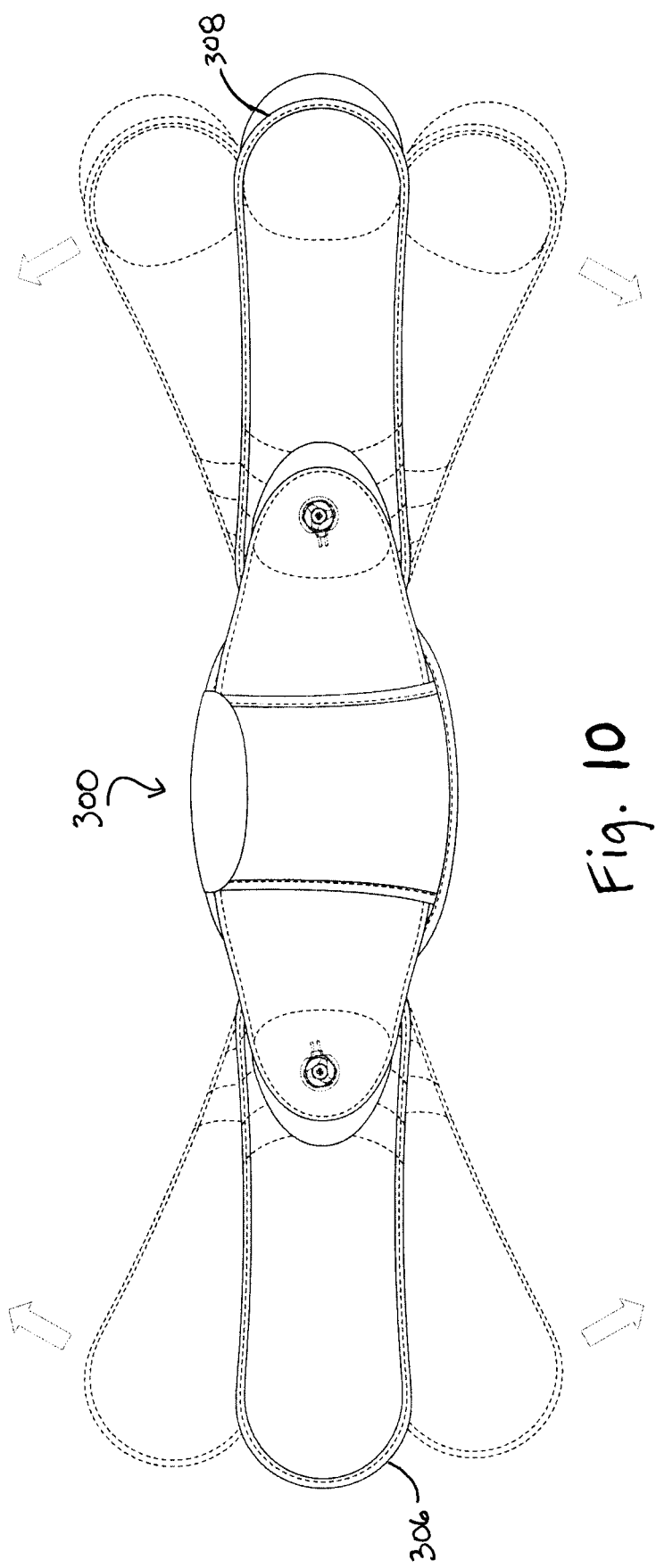

ORTHOPEDIC BACK BRACE

INCORPORATION BY REFERENCE TO ANY PRIORITY APPLICATIONS

This application is a continuation of U.S. application Ser. No. 13/674,613, filed Nov. 12, 2012, now U.S. Pat. No. 9,655,761, and which is incorporated herein by reference in its entirety. Any and all applications for which a foreign or domestic priority claim is identified in the Application Data Sheet as filed with the present application are hereby incorporated by reference under 37 CFR 1.57.

FIELD OF THE INVENTION

The present invention relates generally to an orthopedic brace. More specifically, the present invention relates to an orthopedic brace to provide support to the lower back of a wearer.

BACKGROUND OF THE INVENTION

Lower back injuries and chronic back pain affect many individuals. One of the most effective means of managing back pain and promoting recovery from injuries and/or surgery, is an orthopedic brace. A wide variety of back braces are available to treat a range of injuries, and generally these braces work by stabilizing the spine and limiting motion so as to provide support to the lower back and promote recovery of injured or repaired tissues. When properly fitted, a back brace can effectively alleviate pain and promote recovery from injury or surgery.

A poorly fitted or uncomfortable back brace is less likely to be worn, thereby reducing patient compliance and rendering the device ineffective. Due to variations in height, weight, body circumference, degree of spine curvature, height and angle of the hips, bone prominence, and other anatomical features, it can be difficult for back braces to fit all users. Ideally, a suitable back brace should be adjustable, customizable, and able to fit a wide range of users. Alternatively, hospitals and care providers must stock a large quantity of braces of different sizes, increasing inventory costs. Achieving a satisfactory fit for such a range of users is challenging due not only to the anatomy around the lower back and hip area, but also because a back brace that is properly fitted while the wearer is standing may shift or otherwise become uncomfortable while sitting, and vice versa. Further, many back braces are removable for bathing or sleeping, and must then be refitted by the wearer without the assistance of a trained medical professional.

A need exists, therefore, for a back brace that can provide necessary support and immobilization of a wearer's lumbar region, while also being adjustable to fit a wide range of wearers and can easily be fitted and adjusted by a wearer without assistance.

SUMMARY OF THE INVENTION

In one embodiment, the present invention comprises an orthopedic brace including a pair of back panels, each having a dorsal end and a lateral end, a closure system, including a tensioning mechanism, a lace, and a plurality of lace guides, the lace being coupled to the tensioning mechanism and guided by the lace guides, wherein at least one lace guide is positioned generally on the dorsal end of each back panel, a pair of front panels, each having a lateral end and a ventral end, wherein the lateral end of each front panel is releasably coupleable to the lateral end of each back panel at a desired angle, and wherein the ventral end of each front panel includes an attachment means configured to allow one of the front panels to releasably attach to the other of the front panels generally over an abdomen of a wearer, and a pocket on the ventral end of at least one of the front panels, the pocket configured to temporarily receive a hand of the wearer to aid in donning the orthopedic brace.

In one embodiment, the present invention comprises a method, including causing an orthopedic brace to be manufactured and made available to a user, the orthopedic brace including a pair of back panels, each having a dorsal end and a lateral end, a closure system, including a tensioning mechanism, a lace, and a plurality of lace guides, the lace being coupled to the tensioning mechanism and guided by the lace guides, wherein at least one lace guide is positioned generally on the dorsal end of each back panel, a pair of front panels, each having a lateral end and a ventral end, wherein the lateral end of each front panel is releasably coupleable to the lateral end of each back panel at a desired angle, and wherein the ventral end of each front panel includes an attachment means configured to allow one of the front panels to releasably attach to the other of the front panels generally over an abdomen of a wearer, and a pocket on the ventral end of at least one of the front panels. The method further includes providing instructions to the user, comprising fitting the orthopedic brace on a wearer such that the lace is generally positioned over a spine of the wearer, inserting a hand of the wearer into the pocket of the front panel, and overlapping the ventral end of the front panel over the ventral end of the other of the front panels to secure the front panels to one another via the attachment means, and operating the tensioning mechanism to tighten the brace around the wearer.

BRIEF DESCRIPTION OF THE DRAWINGS

The invention may be more completely understood in consideration of the following detailed description of various embodiments of the invention in connection with the accompanying drawings, in which:

FIG. 2A is an elevation view of an outer side of a back brace according to another embodiment of the present invention.

FIG. 2B is an elevation view of an inner side of the back brace of FIG. 2A.

FIG. 2C is an elevation view of a support insert for use with the back brace of FIG. 2A.

FIG. 2D is an elevation view of a lateral support for use with the back brace of FIG. 2A.

FIG. 2E is an elevation view of a support insert for use with the lateral support of FIG. 2D.

FIG. 3A is an elevation view of an outer side of a back brace according to another embodiment of the present invention.

FIG. 3B is an elevation view of an inner side of the back brace of FIG. 3A.

FIG. 3C is an alternate elevation view of an inner side of the back brace of FIG. 3A.

FIG. 3D is an elevation view of an anterior support insert for use with the back brace of FIG. 3A.

FIG. 3E is an elevation view of a partially disassembled back panel of the back brace of FIG. 3A.

FIG. 4A is an elevation view of an outer side of a back brace according to another embodiment of the present invention.

FIG. 4B is an elevation view of an inner side of the back brace of FIG. 4A.

FIG. 4C is an alternate elevation view of an inner side of the back brace of FIG. 4A.

FIG. 4D is an elevation view of a posterior support insert for use with the back brace of FIG. 4A.

FIG. 4E is an elevation view of a partially disassembled posterior pad for use with the back brace of FIG. 4A.

FIG. 5B is an elevation view of an inner side of the back brace of FIG. 5A.

FIG. 5C is an elevation view of an anterior support insert for use with the back brace of FIG. 5C.

FIG. 5D is an elevation view of a lateral support for use with the back brace of FIG. 5A.

FIG. 6A is an elevation view of an outer side of back panels having an alternate closure system arrangement.

FIG. 6B is a detailed elevation view of a portion of the closure system of the embodiment depicted in FIG. 6A.

FIG. 6C is a detailed elevation view of a lace guide according to the embodiment of FIG. 6A.

FIG. 7A is an elevation view of an outer side of a back brace according to an alternate embodiment of the present invention.

FIG. 7B is an elevation view of an inner side of the back brace of FIG. 7A.

FIG. 8A is an elevation view of an outer side of a back brace according to another embodiment of the present invention.

FIG. 8B is an elevation view of an inner side of the back brace of FIG. 8A.

FIG. 8C is an elevation view of a lateral support insert for use with the back brace of FIG. 8A.

FIG. 8D is an elevation view of an attachment mechanism for use with a posterior pad of the back brace of FIG. 8A.

FIG. 8E is an elevation view of a posterior support insert for use with the back brace of FIG. 8A.

FIG. 8F is an elevation view of an anterior support insert for use with the back brace of FIG. 8A.

FIG. 9A is an exploded elevation view of an outer side of a back brace according to another embodiment of the present invention.

FIG. 9B is an exploded elevation view of an inner side of the back brace of FIG. 9A.

FIG. 10 is an elevation view of an outer side of a back brace according to an embodiment of the present invention, depicting the range of attachment angles of the front panels to the back panels.

Figure 1A:
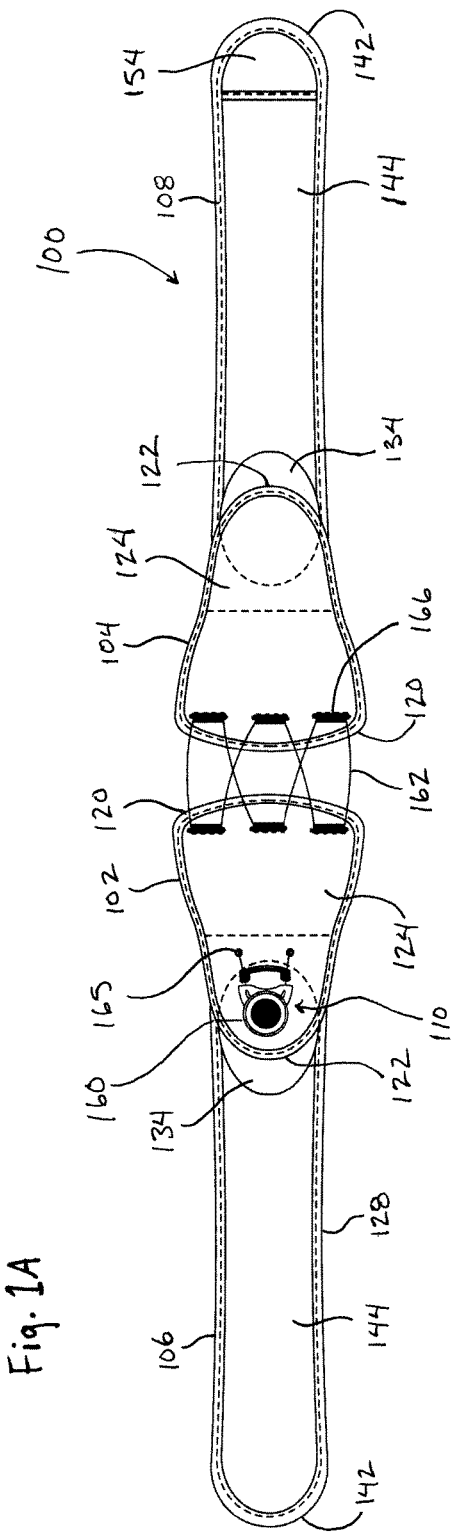
FIG. 1A is an elevation view of an outer side of a back brace according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

Embodiments of the present invention generally include first and second back panels adjustably coupled via a closure system, and first and second front panels releasably attachable to one other via attachment means.

Figure 1B:
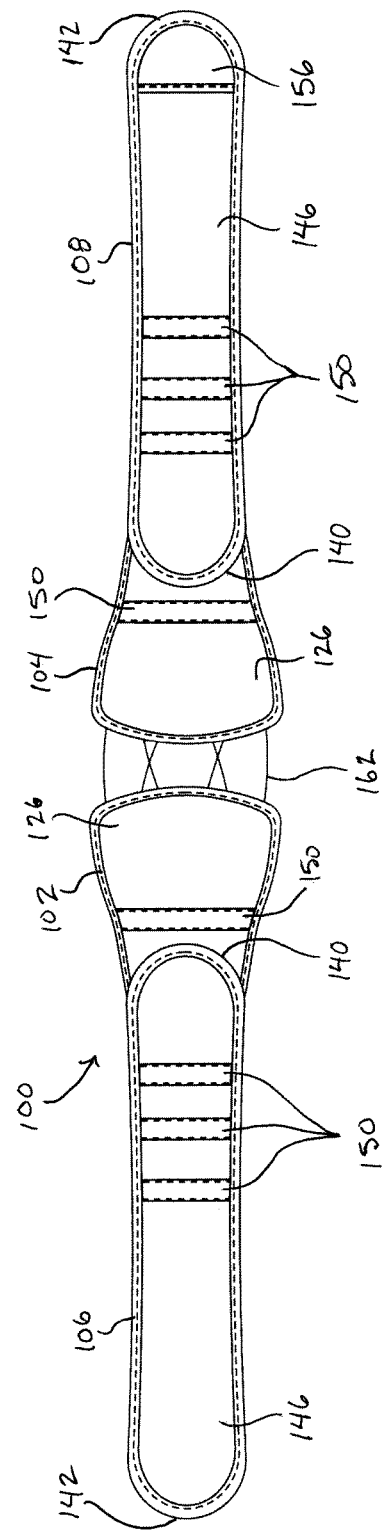
FIG. 1B is an elevation view of an inner side of the back brace of FIG. 1A.
Figure 1C:
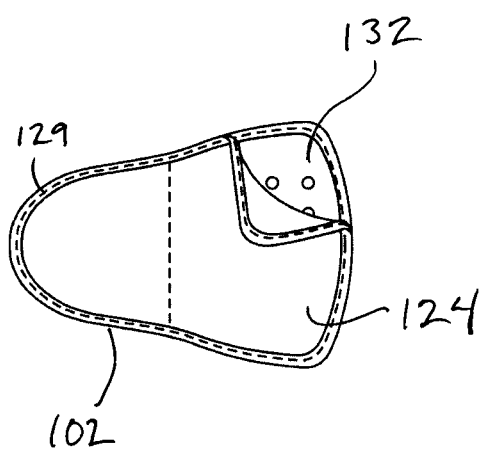
FIG. 1C is an elevation view of a partially disassembled back panel of the back brace of FIG. 1A.

Referring now to FIGS. 1A-1C, a back brace 100 is depicted, which is configured for use as a sacroiliac belt. Back brace 100 includes a first back panel 102, a second back panel 104, a first front panel 106, a second front panel 108, and a closure system 110. Each of back panels 102 and 104 includes a dorsal end 120, a lateral (side) end 122, an outer face 124 and an inner face 126. Back panels 102 and 104 are configured such that the dorsal ends 120 of each back panel are proximate one another and capable of being positioned on the lower back of a wearer, with the back panels 102, 104 capable of wrapping around the wearer such that the lateral ends 122 of each panel 102, 104 are generally positioned on the side of the wearer. Dorsal end 120 of each back panel 102, 104 may include a support 132. As depicted in FIG. 1C, support 132 is secured within the structure of back panels 102, 104 such as by sewing or gluing. In another embodiment, back panels 102, 104 may be provided with a pocket such that support 132 may be removable.

Generally, each of back panels 102, 104 and front panels 106, 108 are constructed of multiple layers of material. In one embodiment, the outer face/layer comprises unbroken-loop ("UBL") fabric, a middle layer comprises closed-cell foam, and the inner face/layer comprises tricot nylon. In one embodiment, one or more of the layers may be constructed of a stretchable material. In another embodiment, none of the layers are of a stretchable material. Additional layers of material may also be added as desired, such as spacer fabric, reinforcing material, waterproofing material, and/or additional foam layers for padding. The outer, middle and inner layers may be joined at their edges, such as by sewing, gluing, thermal or chemical bonding, or other suitable methods. Durable binding fabric 128, such as grosgrain, is sewn around the edge of the panels to provide additional strength. Stitching 129 is utilized generally in construction of many portions of brace 100, as is apparent from the Figures.

In one embodiment, support 132 is constructed from a thermoformable polymer material as described in commonly assigned. Provisional Patent Application No. 61/677,779, filed Jul. 31, 2012 and titled "Foam Core Sandwich Splint" or in commonly assigned U.S. Published Patent Application No. 2012/0101417 to Joseph, the disclosures of which are hereby incorporated by reference in their entireties. The thermoformable material is heat formable within a target temperature range, and rigid or generally rigid below a minimum temperature. In various embodiments, the target temperature range may comprise between 140 and 250 degrees Fahrenheit, between 160 and 220 degrees Fahrenheit, or between 160 and 200 degrees Fahrenheit. The minimum temperature may be about 160 degrees Fahrenheit, or about 150 degrees Fahrenheit, or about 140 degrees Fahrenheit, or about 130 degrees Fahrenheit. Alternatively, support 132 may comprise polyvinyl chloride ("PVC") sheet or foam, amorphous polyethylene terephthalate ("APET"), recycled polyethylene terephthalate ("RPET"), polycaprolactone, caprolactone, low density polyethylene ("LDPE"), high density polyethylene ("HDPE"), or other materials known to one of ordinary skill in the art.

In one embodiment, support 132 may be preformed to a desired shape before application of the back brace to a wearer. Support 132 may include multiple layers of material, for example one or more layers of foam or fabric may be included in addition to a thermoformable material layer. Support 132 may also include two or more layers of thermoformable material, which may be thermoformable at similar temperatures, or which may be thermoformable at different temperatures. For example, support 132 may comprise a first layer of HDPE which is thermoformable at a relatively high temperature in the range of 300 to 400 degrees Fahrenheit and has a thickness of 0.05-1.0 mm, and a second layer of thermoformable material as described in the applications incorporated by reference above and having a thickness of 1.0-1.5 mm. The support may be heated to within a range to thermoform the first HDPE layer, and formed to a desired general shape. After allowing the support to cool to room temperature, the support may then be heated to a temperature within the range to thermoform the second thermoformable layer only, the support can then be formed to a more specific desired shape. Provided the second thermoformable layer is stronger than the first HDPE layer, the support will take the specific desired shape. The shape of support 132 may be reset by heating support 132 to within the range of thermoformability of the HDPE layer.

Each of front panels 106, 108 includes a lateral (side) end 140, a ventral end 142, an outer face 144 and an inner face 146. Front panels 106, 108 are configured so that the lateral end 140 is releasably coupleable to the lateral end 122 of back panels 102, 104, such that front panels 102, 104 will extend generally from the side of a wearer around the front of a wearer with ventral ends 142 of each front panel 106, 108 being releasably coupleable to one another.

A plurality of grip strips 150 are provided on inner face 146 of front panels 106, 108, to prevent shifting of back brace 100 on a wearer, as depicted in FIG. 1B. Grip strips 150 may comprise silicone, rubber, or other suitable materials known to one skilled in the art. Strips 150 may be arranged in other shapes or configurations than those depicted.

The ventral end 142 of one or both front panels 106, 108 may be provided with a mitten pocket 154 on outer face 144. Pocket 154 is sized and shaped to receive a portion or all of a wearer's hand, so as to provide an aid when donning the back brace. Additionally, attachment means 156 in the form of hook-and-loop-compatible material may be provided on ventral end 142 of one or both front panels 106, 108 on outer face 144 and inner face 146 to facilitate attachment of front panel 106 overlapping front panel 108, or vice versa. In one embodiment, at least a portion of inner face 146 of each panel 106, 108 may include hook material on ventral end 142 to interface with the UBL fabric comprising outer face 144 of panels 106, 108.

In one embodiment, each of back panels 102, 104 include attachment means 134 on the inner face 126 of lateral end 122. Attachment means 134 are configured to releasably couple back panels 102, 104 to front panels 106, 108 via attachment means 152 on outer face 144 of side panels 106, 108. Attachment means 134 may comprise any fasteners suitable for use on an orthopedic brace, including but not limited to snaps, buttons, hook-and-loop material, or other suitable fasteners as would be apparent to one skilled in the art. As depicted in FIG. 1A, attachment means 134 comprises hook material, which can interface with the UBL fabric comprising attachment means 152 on outer face 144 of front panels 106, 108. In another embodiment, a tether or other supplemental restraint (not pictured) may be provided as part of attachment means 134, so as to prevent complete separation of back panels 102, 104 from front panels 106, 108 while still allowing front panels 106, 108 to be repositioned as desired.

Referring now to closure system 110, closure system 110 generally comprises a reel 160 secured to outer face 124 of back panel 102 or 104, and one or more laces 162 coupled to reel 160. Lace 162 is fed beneath outer face 124 and into guide tubes 164 (not shown), emerging at the edge of dorsal end 120 through eyelets 165 before being wound through guides 166. As depicted in FIG. 1A, guides 166 are positioned on outer face 124, but in another embodiment guides 166 may be located within the structure of back panels 102, 104. Guides 166 may comprise loops of sturdy material, such as nylon webbing. In one embodiment, webbing guides 166 are provided with an internal guide having a generally arcuate profile, to reduce the friction on lace 162.

One or more components of closure system 110 may be configured to provide a mechanical advantage. For example, reel 160 may be sized and configured to provide a mechanical advantage of about 2:1, or of about 3:1, or of about 4:1, wherein the advantage is determined by the ratio of the circumference of the reel to the circumference of the spool (not pictured) around which lace 162 is wound. Each of guides 166 may be sized and positioned to provide a mechanical advantage of about 2:1, or of about 3:1, or of about 4:1. In one embodiment, closure system 110 includes a reel having a mechanical advantage of 2:1, and three guides 166 each having a mechanical advantage of 2:1, for an overall closure system mechanical advantage of 18:1. Other arrangements are within the scope of the present invention.

Reel 160 is configured to mechanically tighten lace 162 and lock it in place, yet be quickly and easily released. Reel 160 may be of the type available from Boa Technology, which allows laces 162 to be drawn into reel 160 by rotating reel 160 and thereby tightening the fit of brace 100, and also allows tension on laces 162 to be released by pulling on reel 160. The area proximate the attachment point of reel 160 may be strengthened or otherwise reinforced to prevent buckling or distortion of back brace 100 when tightening reel 160. Additional information on reels, laces, lace guides and closure systems in general that are suitable for use with the present invention may be found in U.S. Pat. Nos. 5,934,599, 6,202,953, 6,289,558, 7,950,112, 7,954,204, 7,992,261, and 8,091,182, the disclosures of which are incorporated by reference herein. The use of a reel as part of the closure system may be advantageous to patients who lack the strength and/or flexibility to effectively operate a pull-type closure system such as is found in the prior art, for example in U.S. Pat. No. 7,001,348 to Garth et al. The '348 patent utilizes a pull tab on each side of the brace, which in order to tighten require a patient to reach around their side to grasp the tab, pull the tab outward from their body with enough force so as to create sufficient compression on the lower back region to treat the condition for which the brace was prescribed, and then secure the tab to the body of the brace. This procedure is then repeated for the second pull tab, and the overall procedure that may be difficult for many patients experiencing lower back pain and/or injury. While the use of a reel is advantageous for at least the reasons described above, it will be appreciated by those skilled in the art that other fastening mechanisms such as cord locks, cam cord locks, traditional lacing bows, ratchet lace systems, or other lacing methods may be used in place of any of the closure systems described herein.

Referring now to FIGS. 2A-2E, an alternate embodiment of brace 100 is depicted. Back brace 301 includes an alternate closure system 111, an anterior insert 159, and a plurality of lateral panels 192. Closure system 111 is similar in many respects to closure system 110 of FIGS. 1A-1C, but features a plurality of internal lace guides affixed to an internal layer of brace 101, with a plurality of eyelets 165 on the outer face 124 of panels 102, 104. Closure system 111 is of the type depicted in FIGS. 6A-6C, described in further detail below. Anterior insert 159 is configured to be positioned within ventral end 142 of either front panel 106, 108, such as within a pocket provided for such purpose, or such as by sewing during construction of back brace 101, so that when brace 101 is fitted to a wearer, insert 159 is positioned generally on the anterior of the wearer. Each of lateral panels 192 includes a support 193, which, as with insert 159, may be constructed from a thermoformable polymer material, or PVC sheet or foam, APET, RPET, polycaprolactone, caprolactone, LDPE. HDPE, or other materials known to one of ordinary skill in the art. Lateral panels 192 may be constructed from one or materials previously described herein, such as non-stretchable UBL fabric. Lateral panels 192 may attach to back brace 101 via hook-and-loop fastening means, or other suitable means known to those skilled in the art, and may be secured to back panels 102, 104 at any desired position.

Referring now to FIGS. 3A-3E, a back brace 200 is depicted, which is configured for use as a spine brace. Back brace 200 is similar in many respects to back brace 100, and generally includes a first back panel 202, a second back panel 204, a first front panel 206, a second front panel 208, and a closure system 210. Each of back panels 202 and 204 includes a dorsal end 220, a lateral end 222, an outer face 224 and an inner face 226. Back panels 202 and 204 are configured such that the dorsal ends 220 of each back panel are proximate one another and capable of being positioned on the lower back of a wearer, with the back panels 202, 204 capable of wrapping around the wearer such that the lateral ends 222 of each panel 202, 204 are generally positioned on the side of the wearer. Dorsal end 220 of each panel 202, 204 may include a support 232. As depicted in FIG. 3E, support 232 is secured within the structure of back panels 202, 204 such as by sewing or gluing. In another embodiment, back panels 202, 204 may be provided with a pocket such that support 232 may be removable.

Generally, each of back panels 202, 204 and front panels 206, 208 are constructed of multiple layers of material. In one embodiment, the outer face/layer comprises unbroken-loop ("UBL") fabric, a middle layer comprises closed-cell foam, and the inner face/layer comprises tricot nylon. In one embodiment, one or more of the layers may be constructed of a stretchable material. In another embodiment, none of the layers are of a stretchable material. Additional layers of material may also be added as desired. The outer, middle and inner layers may be joined at their edges, such as by sewing, gluing, thermal or chemical bonding, or other suitable methods. Durable binding fabric such as grosgrain may be sewn around the edge of the panels to provide additional strength.

Support 232 may be of a similar construction to support 132 described earlier, and may therefore be constructed from a thermoformable polymer material, or PVC sheet or foam, APET, RPET, polycaprolactone, caprolactone, LDPE, HDPE, or other materials known to one of ordinary skill in the art. In one embodiment, support 232 may be preformed to a desired shape before application of the hack brace to a wearer.

Each of front panels 206, 208 includes a lateral end 240, a ventral end 242, an outer face 244 and an inner face 246. Front panels 206, 208 are configured so that the lateral end 240 is releasably coupleable to the lateral end 222 of back panels 202, 204, such that front panels 202, 204 will extend generally from the side of a wearer around the front of a wearer with ventral ends 242 of each front panel 206, 208 being releasably coupleable to one another.

Brace 200 may also be provided with one or more sizing indicators 253, as depicted in FIGS. 3A-3E. Sizing indicators 253 may comprise stitch lines on outer face 244 and/or inner face 246 of front panels 206, 208, as depicted in FIGS. 3A-3E, or apertures in panels 206, 208, or other means of sizing indicators as will be apparent to those skilled in the art. Other locations and arrangements of sizing indicators 253 are within the scope of the invention.

The ventral end 242 of one or both front panels 206, 208 may be provided with a mitten pocket 254 on outer face 244. Pocket 254 is sized and shaped to receive a portion or all of a wearer's hand, so as to provide an aid when donning the back brace. Additionally, attachment means 256 in the form of hook-and-loop-compatible material may be provided on ventral end 242 of one or both front panels 206, 208 on outer face 244 and inner face 246 to facilitate attachment of front panel 206 overlapping front panel 208, or vice versa. In one embodiment, inner face 246 of each panel 206, 208 may include hook material on ventral end 242 to interface with the UBL fabric comprising outer face 244 of panels 206, 208.

Additionally, ventral end 242 of one or both front panels 206, 208 may be provided with a pocket 258 on either outer face 244 or inner face 246, configured to receive an anterior insert 259, such as depicted in FIGS. 3B-3D. Insert 259 may be constructed from a thermoformable polymer material, or PVC sheet or foam, APET, RPET, polycaprolactone, caprolactone, LDPE, HDPE, or other materials known to one of ordinary skill in the art. FIG. 3C depicts insert 259 partially withdrawn from pocket 258, for the purpose of illustration. Pocket 258 and insert 259 are configured and arranged such that when brace 200 is fitted to a wearer, insert 259 is positioned generally on the anterior of the wearer.

In one embodiment, each of back panels 202, 204 include attachment means 234 on the inner face 226 of lateral end 222. Attachment means 234 are configured to releasably couple back panels 202, 204 to front panels 206, 208 via attachment means 252 on outer face 244 of side panels 206, 208. Attachment means 234 may comprise any fasteners suitable for use on an orthopedic brace, including but not limited to snaps, buttons, hook-and-loop material, or other suitable fasteners as would be apparent to one skilled in the art. As depicted in FIG. 3A, attachment means 234 comprises hook material, which can interface with the UBL fabric comprising outer face 244 of front panels 206, 208. In another embodiment, a tether or other supplemental restraint (not pictured) may be provided as part of attachment means 234, so as to prevent complete separation of back panels 202, 204 from front panels 206, 208 while still allowing front panels 206, 208 to be repositioned as desired.

Referring now to closure system 210, closure system 210 generally comprises a reel 260 secured to outer face 224 of back panel 202 or 204, and one or more laces 262 coupled to reel 260. Lace 262 is fed beneath outer face 224 and into guide tubes 264 (not shown), emerging at the edge of dorsal end 220 through eyelets 265 before being wound through guides 266. As depicted in FIG. 3A, guides 266 are positioned on outer face 224, but in another embodiment guides 266 may be located within the structure of back panels 202, 204. Reel 260 is configured to mechanically tighten lace 262 and lock it in place, yet be quickly and easily released. Reel 260 may be of the type available from Boa Technology, and generally functions as previously described herein. The area proximate the attachment point of reel 260 may be strengthened or otherwise reinforced to prevent buckling or distortion of back brace 200 when tightening reel 260. Closure system 210 may be sized and configured to provide a mechanical advantage, as described above with respect to closure system 110.

Referring now to FIGS. 4A-4E, a back brace 300 is depicted, which is configured for use as a spine brace. Back brace 300 is similar in many respects to earlier-described back brace embodiments, and generally includes a first back panel 302, a second back panel 304, a first front panel 306, a second front panel 308, and a closure system 310. Each of back panels 302 and 304 includes a dorsal end 320, a lateral end 322, an outer face 324 and an inner face 326. Back panels 302 and 304 are configured such that the dorsal ends 320 of each back panel are proximate one another and capable of being positioned on the lower back of a wearer, with the back panels 302, 304 capable of wrapping around the wearer such that the lateral ends 322 of each panel 302, 304 are generally positioned on the side of the wearer. Dorsal end 320 of each panel 302, 304 may include a support 332. As depicted in FIG. 4E, support 332 is secured within the structure of back panels 302, 304 such as by sewing or gluing. In another embodiment depicted in FIGS. 5B, 5D, back panels 302, 304 include a pocket 330 such that support 332 may be removable.

Generally, each of back panels 302, 304 and front panels 306, 308 are constructed of multiple layers of material. In one embodiment, the outer face/layer comprises unbroken-loop ("UBL") fabric, a middle layer comprises closed-cell foam, and the inner face/layer comprises tricot nylon. In one embodiment, one or more of the layers may be constructed of a stretchable material. In another embodiment, none of the layers are of a stretchable material. The outer, middle and inner layers may be joined at their edges, such as by sewing, gluing, thermal or chemical bonding, or other suitable methods. Durable binding fabric such as grosgrain may be sewn around the edge of the panels to provide additional strength.

Support 332 may be of a similar construction to support 132 described earlier, and may therefore be constructed from a thermoformable polymer material, or PVC sheet or foam, APET, RPET, polycaprolactone, caprolactone, LDPE, HDPE, or other materials known to one of ordinary skill in the art. In one embodiment, support 332 may be preformed to a desired shape before application of the back brace to a wearer.

Each of front panels 306, 308 includes a lateral end 340, a ventral end 342, an outer face 344 and an inner face 346. Front panels 306, 308 are configured so that the lateral end 340 is releasably coupleable to the lateral end 322 of back panels 302, 304, such that front panels 302, 304 will extend generally from the side of a wearer around the front of a wearer with ventral ends 342 of each front panel 306, 308 being releasably coupleable to one another.

Brace 300 may also be provided with one or more sizing indicators 353, as depicted in FIG. 4A. Sizing indicators 353 comprise stitch lines on inner face 346 of front panels 306, 308, although other locations and arrangements of sizing indicators 353 are within the scope of the invention.

The ventral end 342 of one or both front panels 306, 308 may be provided with a mitten pocket 354 on outer face 344. Pocket 354 is sized and shaped to receive a portion or all of a wearer's hand, so as to provide an aid when donning the back brace. Additionally, attachment means 356 in the form of hook-and-loop-compatible material may be provided on ventral end 342 of one or both front panels 306, 308 on outer face 344 and inner face 346 to facilitate attachment of front panel 306 overlapping front panel 308, or vice versa. In one embodiment, inner face 346 of each panel 306, 308 may include hook material on ventral end 342 to interface with the UBL fabric comprising outer face 344 of panels 306, 308.

Additionally, ventral end 342 of one or both front panels 306, 308 may be provided with a pocket 358 on either outer face 344 or inner face 346, configured to receive an anterior insert 359, such as depicted in FIGS. 4A-4C. Insert 359 may be constructed from a thermoformable polymer material, or PVC sheet or foam, APET, RPET, polycaprolactone, caprolactone. LDPE, HDPE, or other materials known to one of ordinary skill in the art. Pocket 358 and insert 359 are configured and arranged such that when brace 300 is fitted to a wearer, insert 359 is positioned generally on the anterior of the wearer.

In one embodiment, each of back panels 302, 304 include attachment means 334 on the inner face 326 of lateral end 322. Attachment means 334 are configured to releasably couple back panels 302, 304 to front panels 306, 308 via attachment means 352 on outer face 344 of side panels 306, 308. Attachment means 334 may comprise any fasteners suitable for use on an orthopedic brace, including but not limited to snaps, buttons, hook-and-loop material, or other suitable fasteners as would be apparent to one skilled in the art. As depicted in FIG. 4A, attachment means 334 comprises hook material, which can interface with the UBL fabric comprising outer face 344 of front panels 306, 308. In another embodiment, a tether or other supplemental restraint (not pictured) may be provided as part of attachment means 334, so as to prevent complete separation of back panels 302, 304 from front panels 306, 308 while still allowing front panels 306, 308 to be repositioned as desired.

Referring now to closure system 310, closure system 310 generally comprises a first reel 360 secured to outer face 324 of back panel 302 or 304, a second reel 361 secured to outer face 324 of the other back panel 302 or 304, and a plurality of laces 362, 363 coupled to reels 360, 361, respectively. Laces 362, 363 are fed beneath outer face 324 and into guide tubes 364, emerging at the edge of dorsal end 320 through eyelets 365 before being wound through guides 366. Guides 366 are positioned on outer face 324, but in another embodiment guides 366 may be located within the structure of back panels 302, 304. Reels 360, 361 are configured to mechanically tighten their respective laces and lock them in place, yet be quickly and easily released. Closure system 310 may be sized and configured to provide a mechanical advantage, as described above with respect to other closure system embodiments. Reels 360, 361 are preferably of the type available from Boa Technology, and generally function as previously described herein.

As best depicted in FIG. 6A, lace 362 is configured to tighten a superior (upper) portion of the brace via reel 360, while lace 363 is configured to tighten an inferior (lower) portion of the brace via reel 361. Reel 360 and lace 362 are operable independently of reel 361 and lace 363, allowing variance in the tension of the superior portion of the back brace and the inferior portion of the back brace. Such an arrangement allows the brace to be properly fitted to the shape of the wearer. The area proximate the attachment point of reels 360,361 may be strengthened or otherwise reinforced to prevent buckling or distortion of back brace 300 when tightening reel 360 and/or reel 361.

Brace 300 may include an optional posterior pad 380 to provide additional comfort and/or support to a wearer. Posterior pad 380 may be of a similar construction as is used for panels 302, 304, 306 or 308 discussed above. In one embodiment, pad 380 includes a support 382, which may be of a similar construction to support 132 described earlier, and may therefore be constructed from one or more layers of thermoformable polymer material, or PVC sheet or foam, APET, RPET, polycaprolactone, caprolactone, LDPE, HDPE, or other materials known to one of ordinary skill in the art. Support 382 may be integrated into pad 380, or may be removably coupled to pad 380, such as by book and loop connection or fitting into a pocket on pad 380 (not shown).

Posterior pad 380 may simply be fitted over back brace 300, without being directly attached to back brace 300. In such an arrangement, pad 380 is capable of moving independently of brace 300, for example allowing pad 380 to remain centered over the spine of a patient while brace 300 is being tightened, or allowing pad 380 to slide side-to-side with respect to brace 300 as desired. As depicted in FIGS. 4A and 4E, posterior pad 380 includes a first closure flap 386 and a second closure flap 387 which are configured to retain posterior pad 380 on back brace 300, while still allowing posterior pad 380 to be adjusted and/or moved as desired by the patient. Closure flap 386 may be provided with one portion of a hook-and-loop material, while closure flap 387 is provided with the other portion, although alternate means of coupling flaps 386, 387 are within the scope of the present invention. Posterior pad 380 may also include a smooth surface configured to be in contact with laces 362 upon installation of pad 380 on back brace 300, in order to reduce friction on laces 362 while donning and/or adjusting the fit of back brace 300. Such surface may be included as a separate layer of material in posterior pad 380, or may support 382 itself.

In other embodiments, posterior pad 380 may be provided with an attachment means configured to releasably couple posterior pad 380 to back brace 300. For example, inner face 326 of back panels 302, 304 may comprise UBL fabric while posterior pad 380 is provided with sections of hook material so as to provide a hook-and-loop connection between posterior pad 380 and back brace 300. In another embodiment depicted in FIG. 4C, back brace 300 includes a plurality of sections of loop material 351 attached to back panels 302, 304, such as by sewing or gluing. Posterior pad 380 may then be provided with sections of hook material so as to provide a hook-and-loop connection between posterior pad 380 and back brace 300. A further embodiment of a posterior pad featuring an attachment means is described below in reference to FIGS. 8A-8F.

Figure 5A:
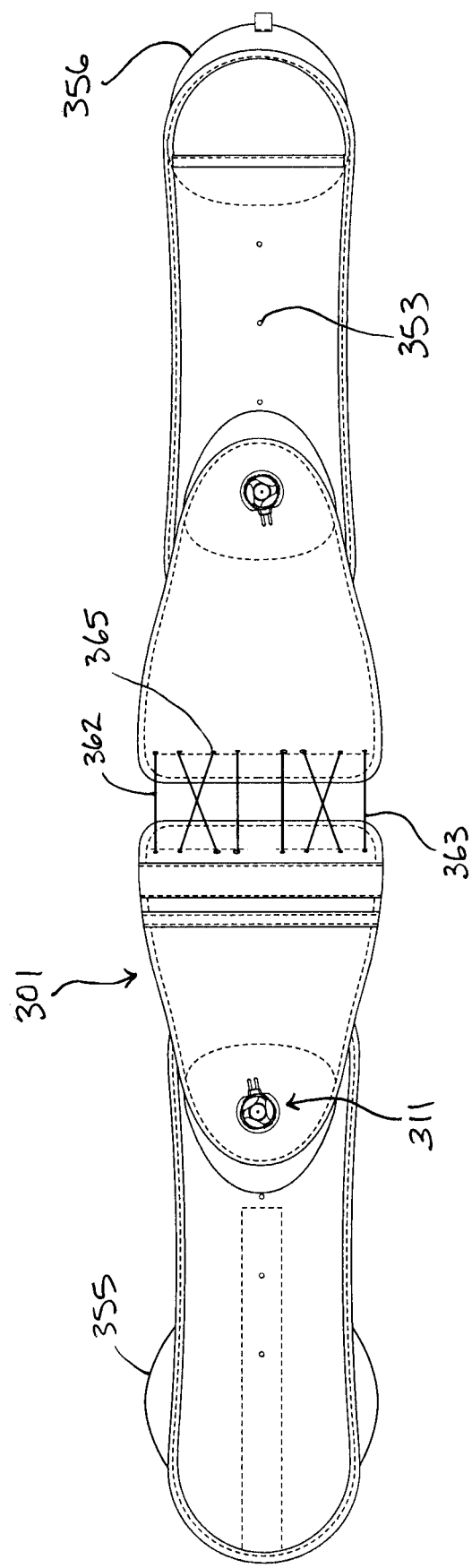
FIG. 5A is an elevation view of an outer side of a back brace according to another embodiment of the present invention.
Figure 7C:
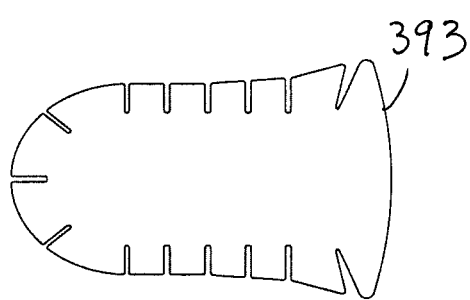
FIG. 7C is an elevation view of a lateral support insert for use with the back brace of FIG. 7A.
Figure 7D:
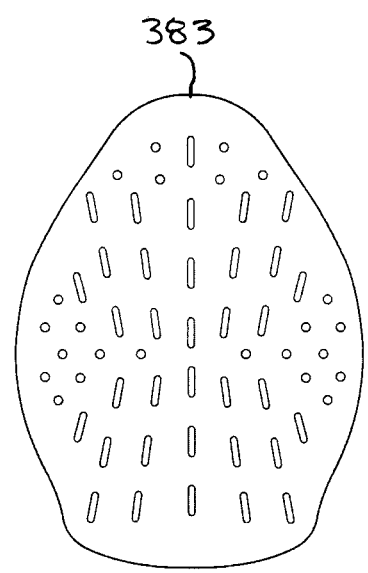
FIG. 7D is an elevation view of a posterior support insert for use with the back brace of FIG. 7A.

Referring now to FIGS. 5A-5D, an alternate embodiment of back brace 300 is depicted. Brace 301 is similar to back brace 300 except as depicted in the Figs., and as described herein. Back brace 301 features an alternate closure system 311 which is similar in many respects to closure system 310 of FIGS. 4A-4E, but differs with a plurality of internal lace guides affixed to an internal layer of brace 301, with a plurality of eyelets 365 on the outer face 324 of panels 302, 304. Closure system 311 is of the type depicted in FIGS. 6A-6C and described in further detail below. Brace 301 also includes a pocket 330 in dorsal end 320 of panel 302 and/or panel 304 to receive support 332. An anterior pad 355 is also provided, being configured to be releasably coupled directly to inner face 346, or a separate attachment feature 357 may be provided, as depicted in FIG. 5B. Alternately, anterior pad 355 may include a layer of UBL fabric, and a component (not pictured) having hook material on both sides may be provided to releasably couple anterior pad 355 to the UBL fabric of inner face 346. Brace 301 also features alternate sizing indicators 353, in the form of holes provided in front panels 306, 308.

Referring now to FIGS. 6A-6C, an alternate closure system 311 is depicted, having a plurality of internal lace guides 368. FIG. 6B depicts middle layer 327 of back panel 302, lacing guide tubes 364, and lace guides 368 secured to reinforcement 328. Each of lace guides 368 generally includes a base portion 369 and a channel 370 through which lace 362 or 363 passes. Channel 370 presents a smooth path of travel for lace 362, in the form of a generally arcuate profile. This closure system could be used in place of any other closure systems described herein, with either single or dual reels.

Referring now to FIGS. 7A-7D, an alternate embodiment of back brace 300 is depicted. Brace 302 is similar in many respects to back braces 300 and 301, except as depicted in the Figs., and as described herein. Back brace 302 features a tall posterior pad 381 and a plurality of lateral panels 392, such that the brace is configured as a chairback brace. Posterior pad 381 includes an internal support 383, and is generally similar in construction and function to posterior pad 380. Lateral panels 392 each include a support 393 within them. Support 393, depicted in FIG. 7C, may be constructed from a thermoformable polymer material, or PVC sheet or foam, APET, RPET, polycaprolactone, caprolactone, LDPE, HDPE, or other materials known to one of ordinary skill in the art. Lateral panels 392 may be constructed from materials previously described herein, such as non-stretchable UBL fabric. Lateral panels 392 may attach to back brace 302 via hook-and-loop fastening means, or other suitable means known to those skilled in the art, and may be attachable to one or more of back panels 302, 304, front panels 306, 308, and/or either side of posterior pad 381 at any desired position.

Referring now to FIGS. 8A-8F, a further alternate embodiment of back brace 300 is depicted. Brace 303 is similar to back braces 300, 301 and 302, except as depicted in the Figs., and as described herein. Back brace 303 features alternate embodiments of posterior pad 381 and lateral panels 392. Posterior pad 381 is generally similar in construction and function to earlier-described embodiments of posterior pads, and includes an internal support 383 and is depicted in FIGS. 8A, 8E without an outer cover over support 383. Brace 303 includes a closure system of the type depicted in FIGS. 6A-6C. An anterior pad 355 is also provided, being configured to be releasably coupled directly to inner face 346, or a separate attachment feature 357 may be provided, as depicted in FIG. 8B. Brace 303 features alternate sizing indicators 353, in the form of holes provided in front panels 306, 308.

Brace 303 further includes alternate embodiments of lateral panels 392 with inserts 393. Lateral panels 392 may be attachable to posterior pad 381, back panels 202, 204, and/or front panels 306, 308 at any desired position. A glide plate 395 is provided to releasably couple posterior pad 381 to brace 303. Glide plate 395 functions as a slider attachment mechanism, and is coupleable to an outer surface of posterior pad 381 at a desired position, and generally includes a pair of attachment means in the form of rivets 396 movably retained within tracks 397. Rivets 396 are of a double-cap type. Other moveable attachment means are within the scope of the invention and will be apparent to one of skill in the art. The dorsal end 320 of each panel 302, 304 may be configured to include a buttonhole so as to receive rivets 396. In operation, posterior pad 381 having glide plate 395 is generally aligned with brace 303, and rivets 396 are passed through corresponding buttonholes in panels 302, 304. The sizing of glide plate 395 and tracks 397 is selected to allow posterior pad 381 to remain properly centered over a wearer's spine during donning and wearing.

Referring now to FIGS. 9A-9B, exploded views of an alternate embodiment of a back brace are depicted. Back brace 304 is similar in most respects to back brace 303, but features alternately profiled anterior pad 355, posterior pad 383, and lateral panels 392.

The features of embodiments of the present invention provide a customizable fit to a wide range of patients of different body types. A method of fitting and adjusting a back brace according to the present invention will now be described in reference to back brace 300 by way of example, although much of the method is applicable to the other embodiments described herein. The order of the steps described below should not be considered limiting, as some steps may be performed in alternate sequences, may be omitted, or may be performed more than once.

Back brace 300 is first extended into a fully open position if necessary, by loosening closure system 310. This may be accomplished by releasing reels 360, 361, such as by pulling outward on a knob portion of the reel. Back panels 302, 304 can then be pulled away from one another. Brace 300 can then be applied to the wearer, generally centering laces 362, 363 over the spine of the wearer. Front panels 306, 308 are then loosely wrapped around the waist of the patient, such that ventral ends 342 of one of front panels 306, 308 sufficiently overlaps the other at the wearer's ventral midline. Mitten pocket 354 may be utilized if desired, to provide additional leverage when wrapping the front panels around the wearer. By way of example only, a sufficient overlap may be within the range of four to eight inches, although this should not be considered limiting. Reels 360, 361 may then be actuated to tighten laces 362, 363, respectively, drawing back panels 302, 304 toward each other and tightening brace 300 around the wearer.

If necessary, the position of front panels 306, 308, can be adjusted with respect to back panels 302, 304, via the interface between attachment means 334 on back panels 302, 304 and attachment means 352 on front panels 306, 308. One or more of front panels 306, 308 are separated from back panels 302, 304, then repositioned as desired to increase or decrease the circumferential size of (or length of) brace 300, then reattached via the attachment means 334 and 352.

The angle of back panels 302, 304, may be adjusted with respect to one another with the use of reels 360, 361, in order to allow a better fit on certain body types or align the brace to account for any injuries present on the wearer. For example, reel 360 may be tightened more than reel 361 in order to draw the tops of back panels 302, 304 closer to one another compared to the bottom of back panels 302, 304, to provide a good fit of brace 300 around the hips of the wearer.

In addition, the angle of front panels 306, 308 with respect to back panels 302, 304, may also be adjusted if desired to allow a better fit on certain body types or align the brace to account for any injuries present on the wearer. As depicted in FIG. 10, front panels 306, 308 may be attached to back panels 302, 304 via attachment means 334 and 352 at any desired angle.

In embodiments wherein brace 300 includes any thermoformable components, such as supports and/or inserts as described herein, the components should be heated as part of the fitting process. Suitable methods of heating include those described in U.S. Published Patent Application No. 2012/0101417 to Joseph, previously incorporated by reference. The thermoformable components may be removed from brace 300 to be heated separately, or the thermoformable panels may be heated while on the patient with the use of a heat source such as a heat gun, temporarily attached exothermic pack, or other suitable means.

Use of the described adjustment features of back brace 300 will provide a more uniform, consistent fit on the wearer, preventing brace 300 from becoming misadjusted due to walking, sitting/standing, and other normal movements of the wearer.

Once a satisfactory fit of back brace 300 on the wearer has been achieved, brace 300 may be removed in order to trim excess material if necessary from front panels 306, 308 along sizing indicators 353. If desired, various accessories such as insert 359, posterior pads 380 or 381, and/or lateral panels 392 may be attached to brace 300 at a desired position.

In another embodiment, the present invention comprises a kit including a back brace according to one or more of the embodiments described herein, and a set of instructions recorded on a tangible medium for fitting the back brace to a wearer according to the methods described herein. In one embodiment, the instructions may comprise instructions for use (IFU) or directions for use, according to the requirements of one or more regulatory bodies and/or government agencies. The instructions may be intended for a patient, or for a health care professional. Alternatively, the kit may include indications which link a user to electronically accessible instructions.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

The invention claimed is:

1. An orthopedic brace, comprising:
   a pair of back panels, each having a dorsal end and a lateral end;
   a closure system, including
      a first lace coupled to a first tensioning mechanism, the first lace and the first tensioning mechanism configured to control the tension of a superior portion of the orthopedic brace, and
      a second lace coupled to a second tensioning mechanism, the second lace and the second tensioning mechanism configured to control the tension of an inferior portion of the back brace, and each of the first and the second tensioning mechanisms operable independently of the other to adjust the fit of the brace to the wearer; and
   a pair of front panels, each having a lateral end and a ventral end, the lateral end of each front panel is releasably coupleable to the lateral end of each back panel at a desired angle, and the ventral end of each front panel includes an attachment means configured to allow one of the front panels to releasably attach to the other of the front panels generally over an abdomen of a wearer.

2. The orthopedic brace of claim 1, wherein the first tensioning mechanism comprises a first reel attached to an outer surface of a first back panel of the pair of back panels, the first reel configured to provide a mechanical advantage determined by a ratio of the circumference of the first reel to a circumference of a first spool around which the first lace is wound.

3. The orthopedic brace of claim 2, wherein the second tensioning mechanism comprises a second reel attached to an outer surface of a second back panel of the pair of back panels, the second reel configured to provide a mechanical advantage determined by a ratio of the circumference of the second reel to a circumference of a second spool around which the second lace is wound.

4. The orthopedic brace of claim 1, further comprising a posterior pad configured to be releasably coupled to at least one of the back panels.

5. The orthopedic brace of claim 4, further comprising a glide plate including a plurality of moveable attaching means, the glide plate releasably coupled to the posterior pad, and the moveable attaching means configured to releasably couple the posterior pad to the back panels.

6. The orthopedic brace of claim 1, further comprising a posterior pad configured to be fitted over at least one of the back panels without being directly coupled to the back panel.

7. The orthopedic brace of claim 1, further comprising at least one lateral support panel configured to be releasably coupled to the orthopedic brace.

8. The orthopedic brace of claim 1, further comprising a posterior pad and at least one lateral support panel configured to be releasably coupled to the posterior pad.

9. The orthopedic brace of claim 1, wherein at least one back panel or at least one front panel includes a thermoformable material, which is heat formable within a range of about 160 and 220 degrees Fahrenheit.

10. The orthopedic brace of claim 1, further comprising an anterior support configured to be releasably coupled to the orthopedic brace.

11. A method, comprising:
    providing an orthopedic brace to a wearer, the orthopedic brace including:
       a pair of back panels, each having a dorsal end and a lateral end, and a closure system, including
          a first lace coupled to a first tensioning mechanism, the first lace and the first tensioning mechanism configured to control the tension of a superior portion of the orthopedic brace, and
          a second lace coupled to a second tensioning mechanism, the second lace and the second tensioning mechanism configured to control the tension of an inferior portion of the back brace, and each of the first and the second tensioning mechanisms being operable independently of the other to adjust the fit of the brace to the wearer, and
       a pair of front panels, each having a lateral end and a ventral end, the lateral end of each front panel releasably coupleable to the lateral end of each back panel at a desired angle, and the ventral end of each front panel including an attachment means configured to allow one of the front panels to releasably attach to the other of the front panels generally over an abdomen of a wearer; and
    operating the tensioning mechanism to tighten the orthopedic brace around the wearer.

12. The method of claim 11, wherein the orthopedic brace includes a first thermoformable material that is thermoformable within a first target temperature range, and wherein the method further comprises heating the thermoformable material to a temperature within the target temperature range.

13. The method of claim 12, wherein heating the thermoformable material comprises heating the thermoformable material while the brace in on the wearer.

14. The method of claim 12, wherein heating the thermoformable material comprises heating the thermoformable material separately from the brace.

15. The method of claim 12, wherein the orthopedic brace includes a second thermoformable material, which is thermoformable within a second target temperature range, and wherein the method further comprises:
    heating the second thermoformable material to a temperature within the target temperature range; and
    forming the second thermoformable material to a desired shape while the second thermoformable material is within the second target temperature range.

16. The method of claim 12, wherein the target temperature range is between about 160 and 220 degrees Fahrenheit.

17. The method of claim 12, wherein the method further comprises fitting the orthopedic brace to the wearer while the thermoformable material is within the target temperature range.

18. The method of claim 11, wherein the first tensioning mechanism comprises a first reel attached to an outer surface of a first back panel of the pair of back panels, the first reel configured to provide a mechanical advantage determined by a ratio of the circumference of the first reel to a circumference of a first spool around which the first lace is wound.

19. The method of claim 18, wherein the second tensioning mechanism comprises a second reel attached to an outer surface of a second back panel of the pair of back panels, the second reel configured to provide a mechanical advantage determined by a ratio of the circumference of the second reel to a circumference of a second spool around which the second lace is wound.

20. The method of claim 11, further comprising adjusting the circumference of the orthopedic brace by coupling the lateral ends of the front panels to the lateral ends of the back panels at a desired length.

\* \* \* \* \*